US009139596B2

(12) United States Patent
Boger

(10) Patent No.: US 9,139,596 B2
(45) Date of Patent: Sep. 22, 2015

(54) CYCLIC PRODRUGS OF DUOCARMYCIN ANALOGS

(71) Applicant: The Scripps Research Institute, La Jolla, CA (US)

(72) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/389,448

(22) PCT Filed: Mar. 26, 2013

(86) PCT No.: PCT/US2013/033809
§ 371 (c)(1),
(2) Date: Sep. 30, 2014

(87) PCT Pub. No.: WO2013/148631
PCT Pub. Date: Oct. 3, 2013

(65) Prior Publication Data
US 2015/0057270 A1  Feb. 26, 2015

Related U.S. Application Data

(60) Provisional application No. 61/617,787, filed on Mar. 30, 2012.

(51) Int. Cl.
*C07D 498/06* (2006.01)
*A61K 31/5365* (2006.01)
*C07D 209/62* (2006.01)
*A61K 45/06* (2006.01)

(52) U.S. Cl.
CPC ............. *C07D 498/06* (2013.01); *A61K 45/06* (2013.01); *C07D 209/62* (2013.01)

(58) Field of Classification Search
CPC .................... C07D 498/06; A61K 31/5365
USPC ......................................... 544/89; 514/229.5
See application file for complete search history.

(56) References Cited

U.S. PATENT DOCUMENTS

| 2,902,487 A | 9/1959 | Wallace |
| 2009/0028821 A1 | 1/2009 | Zhao et al. |
| 2011/0112163 A1 | 5/2011 | Boger et al. |

FOREIGN PATENT DOCUMENTS

WO    WO-2013148631 A1    10/2013

OTHER PUBLICATIONS

International Application Serial No. PCT/US2013/033809, International Preliminary Report on Patentability mailed Oct. 9, 2014, 7 pgs.
Wolfe, Amanda L. et al., "A Novel, Unusually Efficacious Duocarmycin Carbamate Prodrug That Releases No Residual Byproduct", *J. Med. Chem.*, 55, (2012), 5878-5886.
International Application Serial No. PCT/US2013/033809, International Search Report mailed Jun. 10, 2013, 2 pgs.
International Application Serial No. PCT/US2013/033809, Written Opinion mailed Jun. 10, 2013, 5 pgs.
Vacondio, et al., "Qualitative structure-metabolism relationships in the hydrolysis of carbamates", Drug Metabolism Reviews, vol. 42(4), abstract; p. 577, Table 8; p. 581, col. 2, para 3—p. 582, col. 1, para 1, [Online]. Retrieved from the Internet: <http://www.informahealthcare.com>, (2010), 551-589.

*Primary Examiner* — Kahsay Habte
(74) *Attorney, Agent, or Firm* — Geoffrey K. Cooper; Steven M. Reid; Thomas Fitting

(57) ABSTRACT

The invention provides prodrugs of DNA-reactive analogs of duocarmycin and CC-1065 anticancer agents, wherein a cyclic prodrug form, such as carbamate, thionocarbamate, or carbamimidate, can be hydrolyzed by the patient in vivo to yield a respective bioactive agent comprising a DNA-alkylating moiety and a binding/targeting moiety. The DNA-reactive moiety is a γ-spirocyclohexenone fused to a heterocyclyl group which can be produced by endogenous hydrolysis of a cyclic carbamate prodrug of the invention. The cyclic carbamate prodrug produces no residual byproduct during activation in vivo. Methods of synthesis and biological methods and data are also provided.

17 Claims, 1 Drawing Sheet

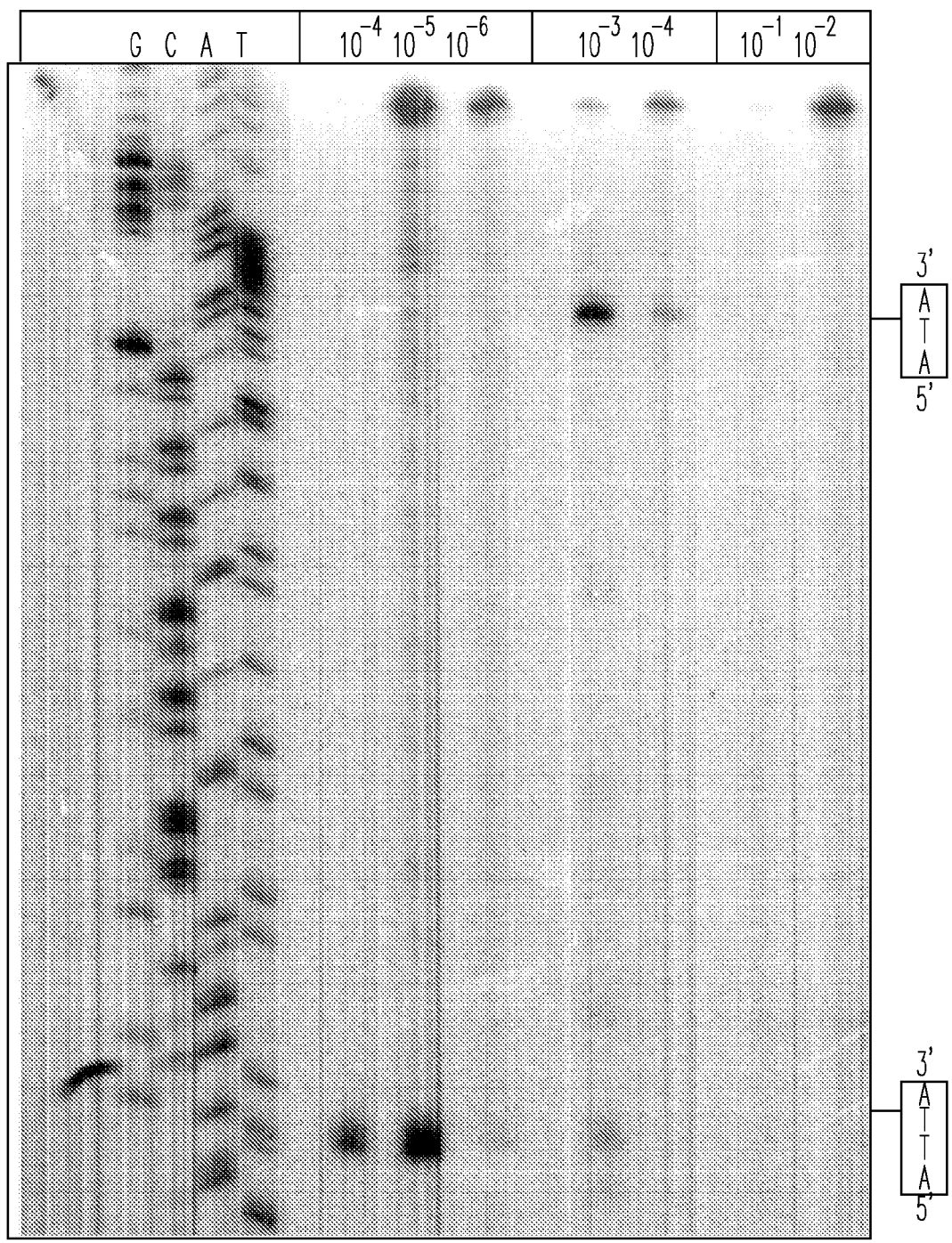

CYCLIC PRODRUGS OF DUOCARMYCIN ANALOGS

CROSS-REFERENCE TO RELATED APPLICATIONS

This application is a U.S. national stage application filed under 35 U.S.C. §371 from International Application Serial No. PCT/US2013/033809, which was filed Mar. 26, 2013, and published as WO 2013/148631 on Oct. 3, 2013, and which claims the priority of U.S. provisional application Ser. No. 61/617,787, filed Mar. 30, 2012, which applications and publication are incorporated by reference as if reproduced herein and made a part hereof in their entirety, and the benefit of priority of each of which is claimed herein.

STATEMENT OF GOVERNMENT SUPPORT

This invention was made with government support under grant number CA041986, awarded by the National Institutes of Health. The U.S. government has certain rights in the invention.

BACKGROUND

Duocarmycin SA (1)[1] and CC-1065 (2)[2] are two parent members of a class of highly potent naturally occurring antitumor agents that also include duocarmycin A[3] and yatakemycin[4] (FIG. 1). This unique class of natural products derives its antitumor properties from their ability to alkylate DNA in a sequence selective manner.[5,6] Comprehensive studies of the natural products, their synthetic unnatural enantiomers,[7] and key analogues have defined many of the fundamental features that control the DNA alkylation selectivity, efficiency, and catalysis, resulting in a detailed understanding of the relationships between structure, reactivity, and biological activity.[6,7,8]

CBI (1,2,9,9a-tetrahydrocyclopropa[c]benz[e]indol-4-one):

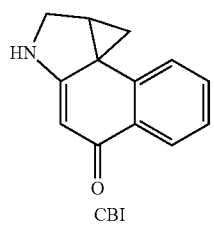

CBI is one of the most extensively studied synthetic analogues of the family since we first introduced it in 1989.[9] The CBI alkylation subunit is not only more synthetically accessible and participates in the now characteristic DNA alkylation reaction effectively,[10] but it has also been found to be 4 times more stable and 4 times more potent than the naturally occurring alkylation subunit of CC-1065 (2), approaching the stability and potency of the duocarmycin SA (1) alkylation subunit. Since analogues incorporating the CBI alkylation subunit have also been established to exhibit efficacious in vivo antitumor activity in animal models, it is an excellent synthetic replacement on which to examine the structure-function features of the natural products, including new prodrug design and evaluation.[11]

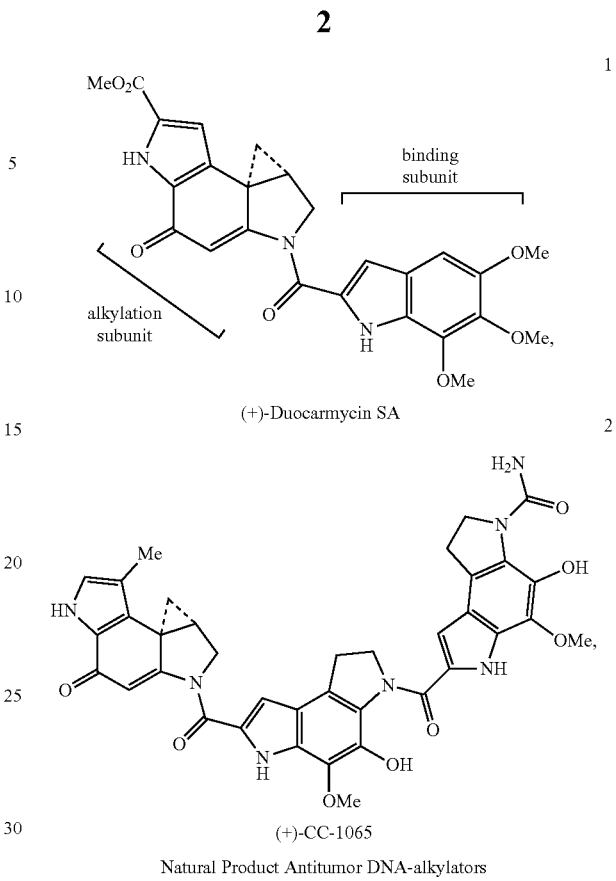

Natural Product Antitumor DNA-alkylators

During the course of the total syntheses of CC-1065 (2), duocarmycin SA (1), duocarmycin A, yatakemycin, and related analogues including CBI-indole$_2$ (5),[11c] it was established that the synthetic phenol precursors such as 4, which have yet to undergo the Winstein Ar-3' spirocyclization, are equipotent to and indistinguishable from their cyclized cyclopropane containing counterparts within in vitro cytotoxic assays, DNA alkylation studies, and in vivo antitumor models.

Scheme 1:
Hydrolysis and Spirocyclization of Acyclic Carbamate Prodrugs 3a-3f

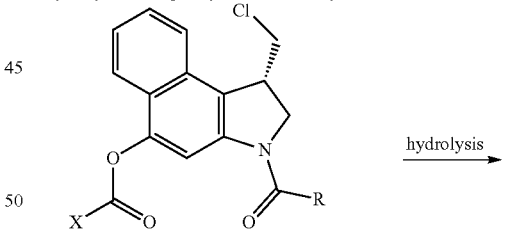

X = 3a, NHMe
3b, NMe$_2$
3c, Me
3d, NHPh
3e,

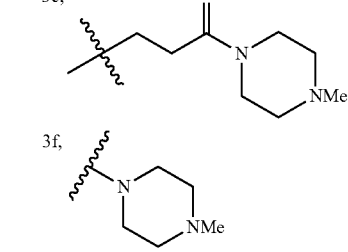

3f,

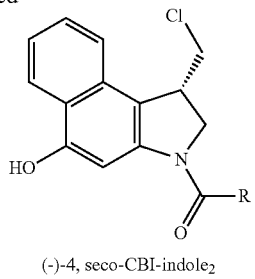

(-)-4, seco-CBI-indole$_2$ spirocyclization ↓

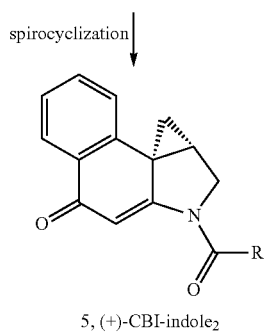

5, (+)-CBI-indole$_2$

R =

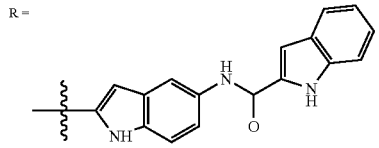

Due to this indistinguishable behavior both in vitro and in vivo and because their extraordinary potency creates special precautions for their handling, protection of the phenol precursors not only permits safe handling during their preparation, but it also provides an effective site on which to create prodrugs that can be designed for controlled release in vivo.[12] Such prodrugs incorporating phenol acylation have been developed to simultaneously improve solubility, pharmacokinetics, storage life, handling safety, and efficacy in vivo.[12,13,14] Two such carbamate-based drugs, KW-2189[12c-d] ($t_{1/2}$=20 h, calf serum) and carzelesin (U-80,244, $t_{1/2}$<1 h, human plasma),[12a-b] which are rapidly cleaved in vivo (1-20 h), entered clinical trials but have ultimately not progressed. In related studies, we described ester and carbamate prodrugs 3a-f of (+)-CBI-indole$_2$, many of which were found to be essentially equipotent to (+)-CBI-indole$_2$ (5) in vitro.[12e] However, upon hydrolysis, such prodrug compound necessarily release a byproduct (shown as $R^N$—H below) as well as the active drug in vivo, which can be a cause of concern with respect to possible byproduct toxicity.

This work established that the free drug is rapidly released in a cellular assay and is able to spirocyclize, alkylate DNA, and express its biological activity efficiently in a manner essentially indistinguishable from the free drug itself.

SUMMARY

The invention herein provides, in various embodiments, unique heterocyclic carbamate and related prodrugs of seco-CBI-indole$_2$ a new class of hydrolyzable prodrugs of the duocarmycin and CC-1065 family of natural products. The prodrugs are designed to be activated by hydrolysis of a cyclic carbamate, carbamothioate, or carbamimidate releasing the free drug. The byproduct of the hydrolysis reaction is respectively carbon dioxide, ammonia, or a thiol. Unlike prior carbamate prodrugs examined that are rapidly cleaved in vivo, the cyclic carbamate was found to be exceptionally stable to hydrolysis under both chemical and biological conditions providing a slow, sustained release of the potent free drug. An in vivo evaluation of the prodrug found that its efficacy exceeded that of the parent drug, that its therapeutic window of efficacy versus toxicity is much larger than the parent drug, and that its slow free drug release permitted the safe and efficacious use of doses 150-fold higher than the parent compound.

The present invention is directed, in various embodiments, to cyclic carbamate, carbamothioate, and carbamimidate derivatives of aminophenolic compounds as defined herein, that act as prodrugs for in vivo formation of γ-spiro-cyclopropyl cyclohexenone analogs of DNA-alkylating duocarmycin and related antitumor compounds. The invention is also directed to methods of synthesis of the prodrugs, and to methods of therapeutic use of the compounds in the treatment of tumors and malignancies in mammalian patients.

The invention provides, in various embodiments, a prodrug of formula (I)

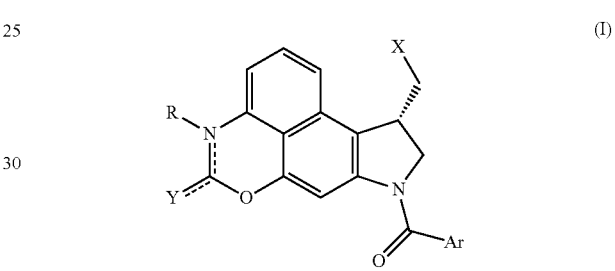

wherein a dotted line indicates a double bond or a single bond, provided that when the N has a double bond thereto, R is absent; X is a leaving group, Y is O, S, SR, or NR, each R is independently H, $(C_1-C_6)$alkyl, or substituted $(C_1-C_6)$alkyl, and Ar is a substituted or unsubstituted heteroaryl; or any salt thereof, or a hydrate thereof. Bioactive prodrugs of the invention possess the "natural" configuration at the chiral carbon (i.e., the carbon bearing the $CH_2X$ group) that corresponds to stereochemical configuration of the natural products duocarmycin and CC-1065. In the above compound of formula (I), when X is halo or is a sulfonate ester, this is the (S)-absolute configuration according to the Cahn-Ingold-Prelog (CIP) priority rules.

Compounds of formula (I) can act as prodrugs through the action of endogenous esterase enzymes, resulting in hydrolysis of the cyclic carbamate, carbamothioate, or carbamimidate group, and the spontaneous formation under in vivo conditions of active DNA-alkylating antitumor agents of the duocarmycin type, which is believed to occur in a manner analagous the following mechanism, shown for Y=O.

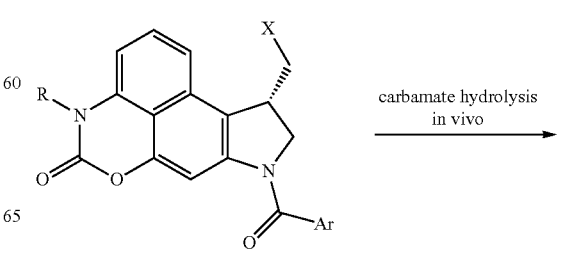

carbamate hydrolysis in vivo

-continued

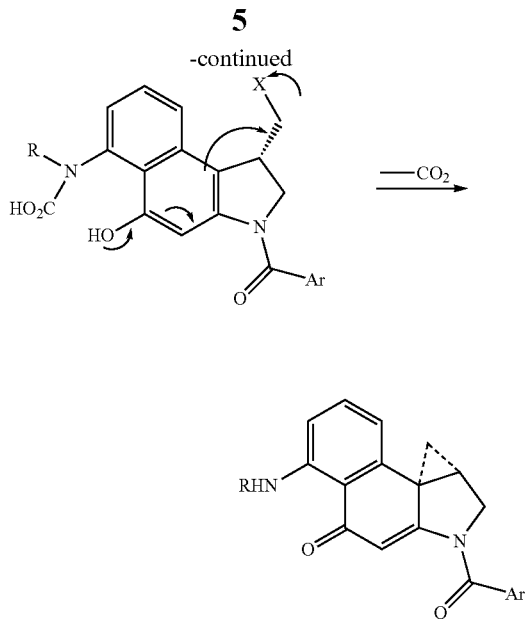

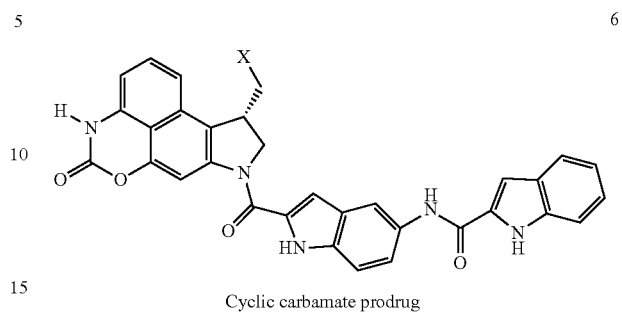

In the spirocyclization reaction shown, the stereochemical configuration of the chiral carbon bearing the CH$_2$X group in the prodrug is conserved; accordingly the absolute configuration of the prodrug is chosen to produce the product having the chiral center unaltered, as shown in the above scheme, although the CIP priority rules may result in a different designation of the configuration under those rules. When Y is S, SR or NR, prodrug ring opening and spirocyclization can occur similarly. In various embodiments, the invention provides novel intramolecular heterocyclic carbamate (+)-CBI-indole$_2$ prodrugs (e.g., compounds 6, see below), and analogs thereof, that are subject to an analogous hydrolysis mechanism of activation,[15] but that are both substantially more stable than acyclic carbamate prodrugs. In the case of the cyclic carbamate and carbamimidate prodrugs, activation does not result in release any extraneous or traceable functionality into the surrounding cellular environment, as only carbon dioxide or ammonia, respectively, is the byproduct. Significantly, the resulting drug is accordingly less potent both in vitro and in vivo, but substantially safer and more efficacious in vivo, effectively taming the extraordinary potency of this class of antitumor drugs.

The invention can provide a prodrug of formula

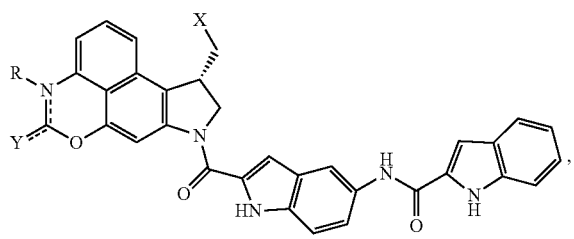

wherein R, X, and Y are as defined herein; or any salt thereof, or a hydrate thereof. X is a leaving group, Y is O, S, SR, or NR, and R is H or alkyl.

For example, the cyclic carbamate prodrug can be of formula 6:

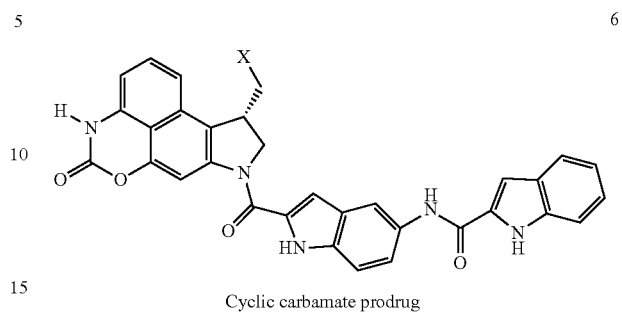

Cyclic carbamate prodrug wherein X is chloro.

An outstanding advantage of the cyclic carbamate prodrugs disclosed and claimed herein is the absence of a byproduct other than carbon dioxide (when Y=O), in the hydrolysis reaction, which occurs in the body tissues of a patient receiving the prodrug in treatment of a tumor or malignancy. Non-cyclic carbamates, wherein cleavage of the carbamate bond brings about release of the amino-bearing functionality as a separate molecular entity byproduct, can raise concerns about side effects of the byproducts released in the body, but the cyclic carbamate initial hydrolysis product is a carbamic acid which spontaneously decarboxylates to give the amino compound and carbon dioxide.

In various embodiments, the invention provides methods of synthesis for compounds of formula (I), as described herein. In various embodiments, the invention provides methods of treatment of tumors and malignancies comprising administering an effective amount of a prodrug of formula (I), or of compound 6, to a patient in need thereof, at a frequency and for a duration of administration sufficient to provide a beneficial effect to the patient, such as slowing tumor growth, inducing remission, or inhibiting metastasis of the tumor.

BRIEF DESCRIPTION OF THE FIGURES

FIG. 1 is an autoradiograph of thermally induced strand cleavage of w794 DNA; DNA-agent incubation at 23° C. for 48 h, removal of unbound agent by EtOH precipitation, and 30 min of thermolysis (100° C.) followed by 8% denaturing PAGE and autoradiography. Lane 1, control DNA; lanes 2-5, Sanger G, C, A, and T sequencing reactions; lanes 6-8, (+)-1 ($1 \times 10^{-4}$ to $1 \times 10^{-6}$); lanes 9-10, (−)-1 ($1 \times 10^{-3}$ to $1 \times 10^{-4}$); lanes 11-12, (+)-6 ($1 \times 10^{-1}$ to $1 \times 10^{-2}$).

DETAILED DESCRIPTION

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions involving tumors, neoplasms, or malignancies, wherein DNA alkylation, e.g., sequence-specific DNA alkylation, can play a role in the therapy for the disease or malcondition or symptom(s) thereof such that a therapeutically beneficial effect can be achieved.

The expression "effective amount", when used to describe therapy to an individual suffering from a disorder, refers to the amount of a compound of the invention that is effective to alkylate DNA in the individual's tissues, such as in the tumor or malignancy, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid or carbamic acid groups, which can be hydrolyzed by endogenous esterases as are found in the bloodstream of humans and other mammals. Endogenous hydrolysis of a carboxylic ester provides an alcohol and an acid; endogenous hydrolysis of a carbamate yields an alcohol, and amine, and carbon dioxide (through decarboxylation of the carbamic acid). Conventional procedures for the selection and preparation of suitable prodrug derivatives are described, for example, in "Design of Prodrugs", ed. H. Bundgaard, Elsevier, 1985. Prodrugs herein are the cyclic carbamates, carbamothioates, and carbamimidates, which undergo hydrolysis under the action of enzymes present in vivo, to yield compounds that can then undergo the spontaneous spirocyclization reaction as described herein to yield the bioactive anticancer agents.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N(R)—Y or X—N(R)C(=O)—Y, unless the context clearly limits the orientation of the group within the molecular structure.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite. For example, "alkyl" can be C1-C4, or C1-C8, or C1-C20 alkyl.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

In various embodiments, J can be halo, nitro, cyano, OR, NR$_2$, or R, or is C(O)OR, C(O)NR$_2$, OC(O)OR, OC(O)NR$_2$, N(R)C(O)OR, N(R)C(O)NR$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S)NR$_2$, and SC(S)NR$_2$; and so forth.

Accordingly, a "substituted" alkyl group is an alkyl group that bears one or more J groups, which can bear R' groups, which R' groups can be further substituted with a group selected from the list of substituents described above.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic.

By "spirocyclic" is meant the class of structures wherein two rings are fused at a single tetrahedral carbon atom, as is well known in the art. A "spirocyclization reaction" refers to a reaction that creates a spiro carbon atom. For example, the following reaction is referred to as a spirocyclization reaction in the present application:

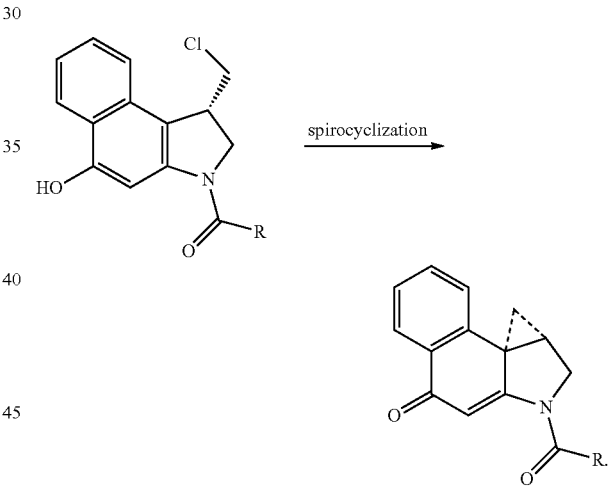

As can be seen, a spiro carbon atom is created at the γ-position of the enone, in a reaction referred to as a "Winstein Ar-3' spirocyclization" or "Winstein spirocyclization."

In the spirocyclization reaction, the phenol is the nucleophile in a nucleophilic substitution reaction wherein the chloro group in the example shown above functions as a leaving group. A "leaving group", or "nucleofugal" group, as the term is used herein refers to a group that departs from a carbon center in a substitution reaction; usually a group that is stable in anionic form such as a halide ion, e.g., a chloride ion in the above-illustrated example. Examples of leaving groups, such as are well known in the art, include halo groups, sulfonate ester groups, and the like.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, thiadiazolyl, pyridinyl, pyrimidinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carb azolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The terms "halo" or "halogen" or "halide" by themselves or as part of another substituent mean, unless otherwise stated, a fluorine, chlorine, bromine, or iodine atom, preferably, fluorine, chlorine, or bromine.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" group is a group of the formula C(O)NR$_2$, wherein R can be H, alkyl, aryl, etc.

A "sulfonate ester", as the term is used herein, refers to an esterified form of an alkylsulfonic acid (e.g., a methanesulfonate, "mesylate"), a haloalkylsulfonic acid (e.g., a trifluoromethylalkylsulfonate, "triflate") an arylsulfonic acid (wherein the aryl group can be substituted, e.g., a p-toluenesulfonate, "tosylate"; p-bromobenzenesulfonate, "brosylate"), and others.

The term "amino protecting group" or "N-protected" as used herein refers to those groups intended to protect an amino group against undesirable reactions during synthetic procedures and which can later be removed to reveal the amine Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromo acetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally nontoxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

It will be understood that when compounds of the present invention contain one or more chiral centers, the compounds may exist in, and may be isolated as single and substantially pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated as having an (R) absolute configuration, and if the descending rank of the other groups proceeds counterclockwise, the molecule is designated as having an (S) absolute configuration. In the example in the Scheme below, the Cahn-Ingold-Prelog ranking is A>B>C>D. The lowest ranking atom, D is oriented away from the viewer.

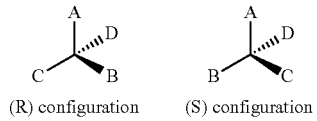

(R) configuration    (S) configuration

A carbon atom bearing the A-D atoms as shown above is known as a "chiral" carbon atom, and the position of such a carbon atom in a molecule is termed a "chiral center."

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

"Isolated optical isomer" or "isolated enantiomer" means a compound which has been substantially purified from the corresponding optical isomer(s) of the same formula. Preferably, the isolated isomer is at least about 80%, more preferably at least 90% enantiomerically pure, even more preferably at least 98% enantiomerically pure, most preferably at least about 99% enantiomerically pure, by weight. By "enantiomeric purity" is meant the percent of the predominant enantiomer in an enantiomeric mixture of optical isomers of a compound. A pure single enantiomer has an enantiomeric purity of 100%.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Another well-known method of obtaining separate and substantially pure optical isomers is classic resolution, whereby a chiral racemic compound containing an ionized functional group, such as a protonated amine or carboxylate group, forms diastereomeric salts with an oppositely ionized chiral nonracemic additive. The resultant diastereomeric salt forms can then be separated by standard physical means, such as differential solubility, and then the chiral nonracemic additive may be either removed or exchanged with an alternate counter ion by standard chemical means, or alternatively the diastereomeric salt form may retained as a salt to be used as a therapeutic agent or as a precursor to a therapeutic agent.

In various embodiments, the invention provides a prodrug of formula (I)

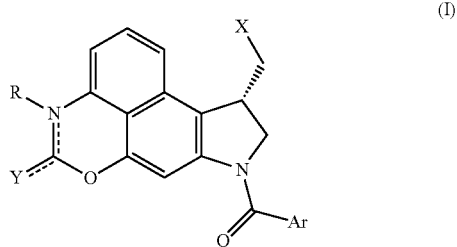

(I)

wherein a dotted line indicates a double bond or a single bond, provided that when the N has a double bond thereto, R is absent;

X is a leaving group, Y is O, S, SR, or NR, each R is independently H, ($C_1$-$C_6$)alkyl, or substituted ($C_1$-$C_6$)alkyl, and Ar is a heteroaryl, which can be substituted or unsubstituted;

or a stereoisomer thereof, or any salt thereof, or a hydrate thereof.

For example, Y can be O, providing a cyclic carbamate:

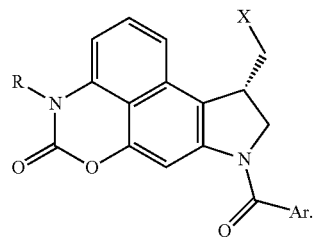

In other embodiments, Y can be S, providing a cyclic carbamothioate:

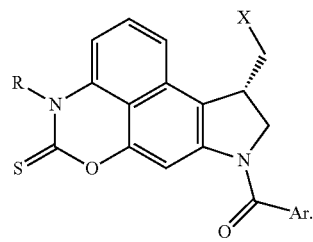

In still other embodiments, Y can be NR, providing a cyclic carbamimidate;

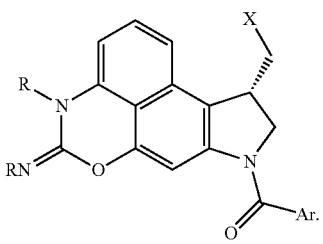

Or Y can be SR, wherein R is alkyl or substituted alkyl. For example, SR can be S-methyl, or can be S—$CH_2CH_2$—$CO_2$-ester, or can be S—$CH_2CH_2$-phthalimido, or the like, providing an S-alkyl-carbamothioate:

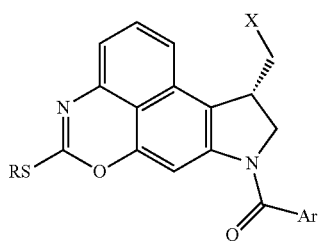

The invention can provide a prodrug of formula

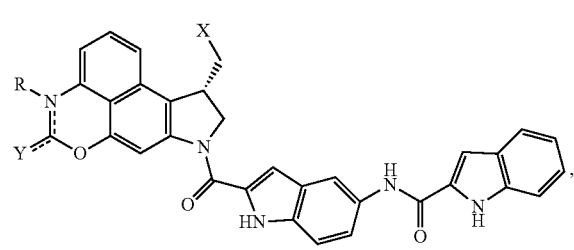

wherein R, X, and Y are as defined herein; or a stereoisomer thereof, or any salt thereof, or a hydrate thereof.

The invention can provide a prodrug of formula

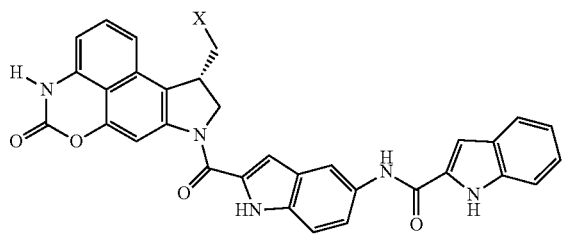

wherein leaving group X is as defined herein.

For example, leaving group X can be a halo, such as a chloro group, or can be a sulfonate ester, such as a mesylate or a triflate. When X is chloro, the prodrug is compound 6

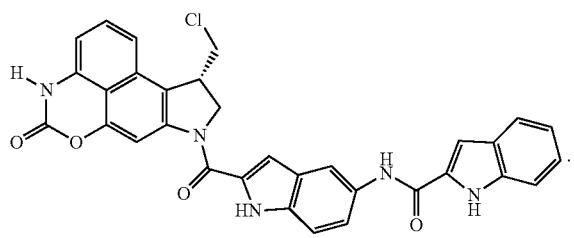

As is apparent, a chiral center is present in compound 6, at the carbon atom bearing the chloromethyl group. The compound as shown is (+)-6, which is the (S)-isomer, which is also referred to herein as the "natural" configuration, i.e., the enantiomeric configuration corresponding to the configuration at the corresponding carbon atom in the natural products duocarmycin and CC-1065.

In various embodiments, the N-substituent of the cyclic carbamate moiety can be hydrogen; alternatively it can be a small, non-sterically hindered alkyl group or the like.

The Ar group is believed to be significant in terms of a targeting or DNA-binding moiety, providing stabilizing interactions with the DNA target molecule such that the reactive alkylating moiety, liberated in vivo by endogenous enzymes from the precursor moiety of the prodrug, can undergo reaction with the DNA. The alkylation reaction of the reactive moiety thus produced can occur with the DNA in proximity to the binding site of the compound to the DNA. This alkylation process is believed to destabilize the DNA thus targeted, which can be cytotoxic to the tumor cells.

Formation of the spiro-cyclopropyl-γ-cyclohexenone moiety via the Winstein spirocyclization reaction, following endogenous liberation of the free phenol group from the cyclic carbamate, carbamothioate, or carbamimidate prodrug moiety, is following by reaction, e.g., alkylation, of specific DNA moieties by this reactive group. Such a mutation can be lethal to the cell containing the DNA target. It is believed that alterations in the Ar group, i.e., in the binding/targeting moiety, can result in different DNA binding specificities of prodrugs of the invention.

In various embodiments, the Ar group comprises one or two indolic moieties. The Ar group can be bonded to the carbonyl group shown attached to the pyrrolidine ring of the benzodihydroindole moiety bearing the chloromethyl (or other methylene group with a leaving group such as a sulfonate ester or the like). For example, Ar can comprise an indole bonded at an indole 2-position, such as in duocarmycin itself, which bears a trimethoxyindole moiety at an analogous position of the targeting moiety. In various embodiments, a first indolyl moiety forming a binding/targeting moiety can be unsubstituted, or can be substituted with various groups as outlined above. In various embodiments, the indole of the Ar group can be further substituted with a heteroaroylamino group. This indole group can be further substituted, such as with a second indolic group, as is present in CC-1065, shown above. Similarly, a second indolic group can be unsubstituted or can be substituted with groups such as outlined above. Either indole, i.e., the first indolic moiety of the Ar group analogous to duocarmycin, or a second indolic moiety as is present in CC-1065, can be an unsubstituted or a substituted indolic group, in various embodiments. In other embodiments, heteroaryl groups other than indole groups can be comprised by the binding/targeting moiety, which, bonded to the prodrug form of the reactive moiety, can be used to target DNA in various manners.

For example, the present application discloses and claims a novel intramolecular heterocyclic carbamate (+)-CBI-indole$_2$ prodrug (6)

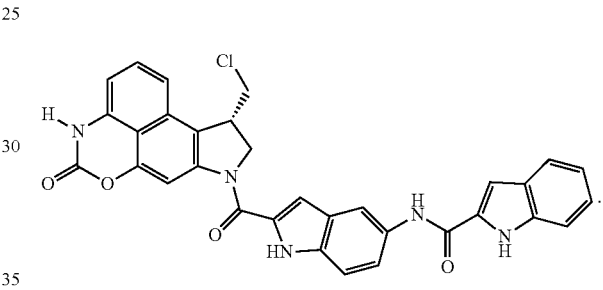

that is subject to the outlined hydrolysis mechanism of activation,[15] but that is both substantially more stable and upon activation does not release any extraneous or traceable functionality into the surrounding cellular environment. Significantly, the resulting drug is accordingly less potent both in vitro and in vivo than is the spiro-cyclized compound, but is substantially safer and more efficacious in vivo, effectively taming the extraordinary potency of this class of antitumor drugs.

According, a prodrug of formula (I) can be cyclic carbamate compound 6, or any salt thereof, or a hydrate thereof. It is believed that in addition to a single indolic moiety at this position analogous to duocarmycin, or the two 2-substituted indoles of compound 6 analogous to CC-1065, other targeting groups, such as other heteroaryl groups, can be disposed in analogous position. Variations in the targeting moiety can lead to different specificities for DNA sequences, or to increases or decreases in binding affinities for particular DNA sequences.

In various embodiments, the invention provides a pharmaceutical composition comprising a prodrug of formula (I) and a pharmaceutically acceptable excipient. More specifically, the prodrug of formula (I) can be the compound of formula 6.

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of*

*Pharmacy*, 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly (anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 μg to about 1250 mg, preferably from about 250 μg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

In various embodiments, the invention provides a method of treatment of a disease, disorder, or malcondition comprising a tumor or a malignancy, for which a course of treatment comprising DNA alkylation is medically indicated, for a patient suffering therefrom, comprising administration of an effective amount of a prodrug of formula (I) of claim 1 to a patient in need thereof, at a frequency and for a duration of administration sufficient to provide a beneficial effect to the patient. For example, the beneficial effect can comprise slowing tumor growth, inducing remission, or inhibiting metastasis of the tumor or malignancy.

Further, a method of the invention can comprise administration to the patient of an effective amount of an anticancer drug. Use of an anticancer drug that operates by a molecular mechanism other than DNA alkylation or other than sequence-specific DNA alkylation can reduce the probability of tumor cells developing resistance to anticancer medicinal therapy. For example, an anticancer drug that can be administered in conjunction with a prodrug of the invention can be another type of DNA-alkylating agent, or can be a monoclonal antibody, or can be a taxane alkaloid, or a Vinca alkaloid, or an anti-metabolite (e.g., cytostatic), or an anthrocycline, or a topoisomerase inhibitor (e.g., an aromatase inhibitor), or an anthracycline such as doxorubicin. See, for example Takimoto C H, Calvo E. "Principles of Oncologic Pharmacotherapy" in Pazdur R, Wagman L D, Camphausen K A, Hoskins W J (Eds) Cancer Management: A Multidisciplinary Approach. 11 ed. 2008.

Evaluations

It is within ordinary skill using the procedures provided herein and in references cited herein, which are incorporated by reference in their entireties, to evaluate any compound disclosed and claimed herein for effectiveness for in vivo evaluation of antitumor activity as well as in the various cellular assays found in the scientific literature. Accordingly, the person of ordinary skill, using the disclosure of the present application in conjunction with the disclosures of documents cited herein, and the knowledge of the person of ordinary skill, can prepare and evaluate any of the claimed compounds for effectiveness as a potential human therapeutic agent, without undue experimentation.

Any compound found to be effective as an antitumor agent can likewise be further tested in animal models, and in human clinical studies, using the skill and experience of the investigator to guide the selection of dosages and treatment regimens.

In various embodiments, the invention provides methods of synthesis of a prodrug of the invention. For example, cyclic carbamate prodrugs of the invention wherein Y═O, cyclic carbamothioate prodrugs wherein Y═S, and cyclic carbamimidate prodrugs wherein Y═NR, (e.g., NH), can be prepared according to the synthetic scheme shown below:

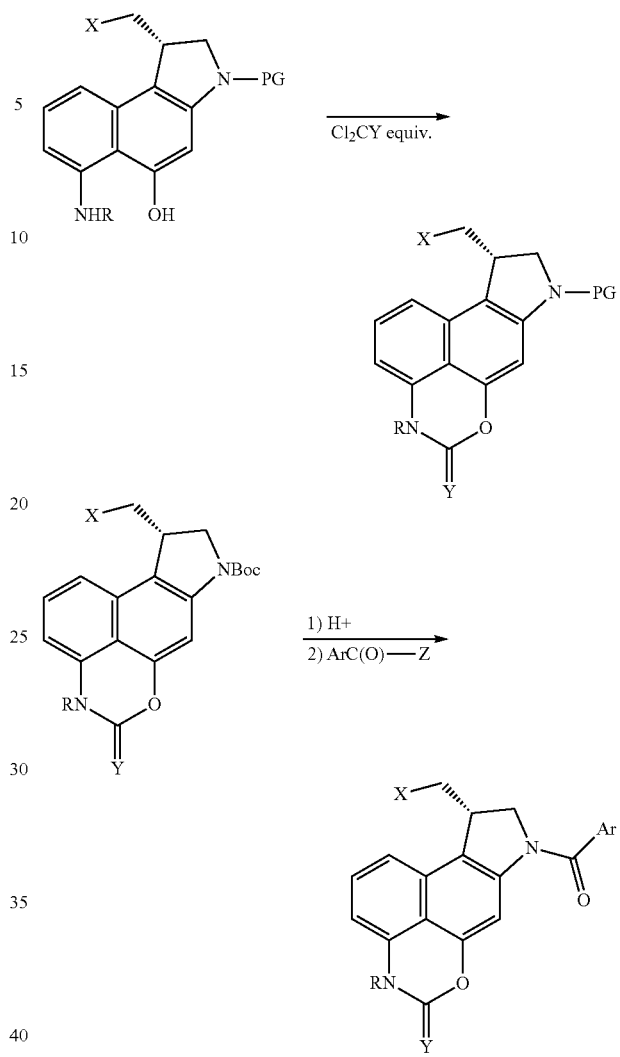

wherein X, Y and Ar are as defined herein. It is understood that a single enantiomer of each intermediate is depicted herein, but that if the opposite enantiomeric form of a prodrug of the invention is desired, the corresponding enantiomeric species can be used in the synthesis as disclosed herein.

For example, cyclic carbamate prodrugs of the invention can be prepared by use of a phosgene equivalent, such as triphosgene, in the first step, and the product carried through the N-protecting group removal and N-acylation of the second step under suitable conditions, examples of which are disclosed herein.

For example, cyclic carbamothioate prodrugs of the invention can be prepared by an analogous sequence, wherein a thiophosgene equivalent is used in the first step, and the product carried through the N-protecting group removal and N-acylation of the second step in an analogous manner. For preparation of an S-alkyl carbamothioate compound (i.e., wherein Y is SR), alkylation of the sulfur atom of the unsubstituted carbamothioate with an alkylating agent such as a halide, sulfonate ester, etc., can provide the prodrug product.

For example, cyclic carbamimidate prodrugs of the invention can be prepared by an analogous sequence, wherein a imidoylating reagent, such as carbonimidic dichloride or an N-alkyl analog thereof, is used in the first step, and the product carried through the N-protecting group removal and N-acylation of the second step in an analogous manner.

In various embodiments, the invention provides key synthetic intermediates useful in carrying out preparation of the prodrugs disclosed and claimed herein.

In the formation of the cyclic carbamate in the first reaction shown above, use of a phosgene equivalent, such as triphosgene, can provide the cyclic carbamate form of the prodrug reactive moiety, and subsequent N-protecting group hydrolysis followed by acylation with a suitable acylating agent, can be used to prepare prodrugs of the invention wherein R and Ar groups are as defined herein. Z can be any suitable carboxyl-activating group, such as the group produced by reaction of a carboxylic acid and a carbodiimide such as EDCI. By selection of a suitable Ar—$CO_2H$ or equivalent group, the binding/targeting moiety of the prodrug can be elaborated. Analogous synthetic sequences can be used in the preparation of carbamothioate and carbamimidate subclasses of the inventive cyclic prodrugs.

It is noted that the manufacture of the cyclic prodrugs can provide enhanced safety and ease of handling of the material, in preparation of a useful medicinal form, in that the cyclic carbamate form is relatively stable and unreactive, compared to an active form of a duocarmycin-like or CC-1065-like material.

Examples

Chemistry

Synthesis

Prodrug (+)-6 was synthesized[16] in 11 steps from known intermediate 7[17] as shown in Scheme 1, below. The phenol of 7 was protected as its benzyl ether and 8 was hydrolyzed to provide the carboxylic acid 9 in good overall yield using LiOH. Carboxylic acid 9 was subjected to a Curtius rearrangement using diphenylphosphoryl azide (DPPA) and $Et_3N$ in freshly distilled t-BuOH providing the Boc protected aniline 10 in 79% yield. The use of non-distilled t-BuOH resulted in low yields due to competing release of the free aniline Regioselective Cl iodination of 10 and subsequent N-alkylation of 11 with 1,3-dichloropropene proceeded effectively, providing the cyclization precursor 12. Finally, a selective 5-exo-trig free radical cyclization[18] of 12 using sub stoichiometric quantities of $Bu_3SnH$ (0.9 equiv) provided 13 in 83% yield with only trace amounts of further reduced (debrominated) material observed.

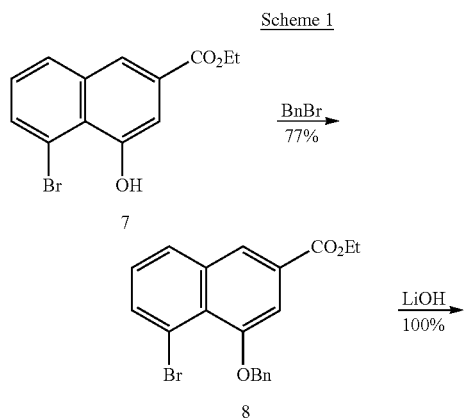

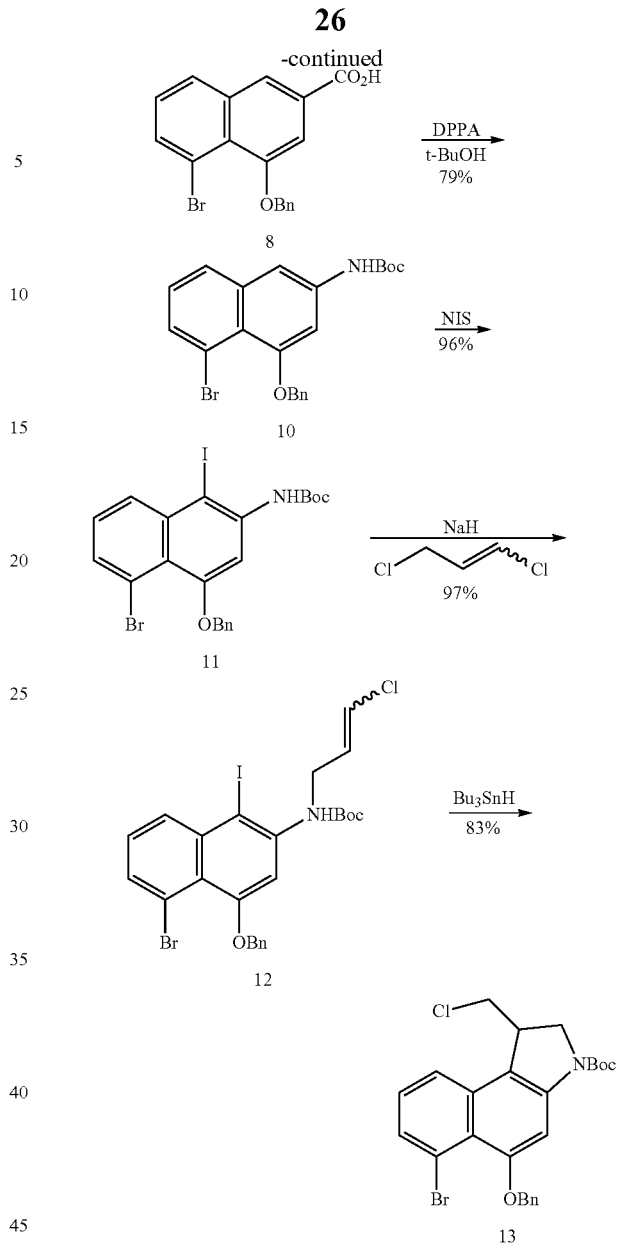

Compound 13, which has served as a key precursor in the divergent synthesis[19] of a series of compounds,[20] was further elaborated to aniline 15 using triphenylsilylamine[21] as an ammonia surrogate for a Pd(0) catalyzed aryl amination[22] with LiHDMS in THF and ligand 14 (Scheme 2). Fortunately, a solution of LiHMDS could be used in place of solid LiHMDS, which alleviated the need for use of a glove box as reported.[22] Other amination reactions, including the use of benzophenone imine and copper-promoted couplings with acetamidine, yielded only trace amounts of the desired amination product. $Bu_4NF$ deprotection of the resulting amine and debenzylation of the phenol under hydrogenation conditions produced aniline 15 Aniline 15 was converted to the cyclic carbamate 16 by a double acylation with triphosgene, which proceeded cleanly and in quantitative yield. At this point, compound 16 was resolved into its two enantiomers using chiral phase HPLC with 20% i-PrOH/hexanes as the eluent. We chose to resolve 16 instead of 6 itself in order to permit access to additional resolved analogues and to avoid the lower solubility of the full prodrug 6 in the chromatography solvents. Each enantiomer of 16 was subjected to Boc deprotection with 4 N HCl in EtOAc and immediate N-acylation with 17, providing (+)- and ent-(−)-6 in 52% yield.

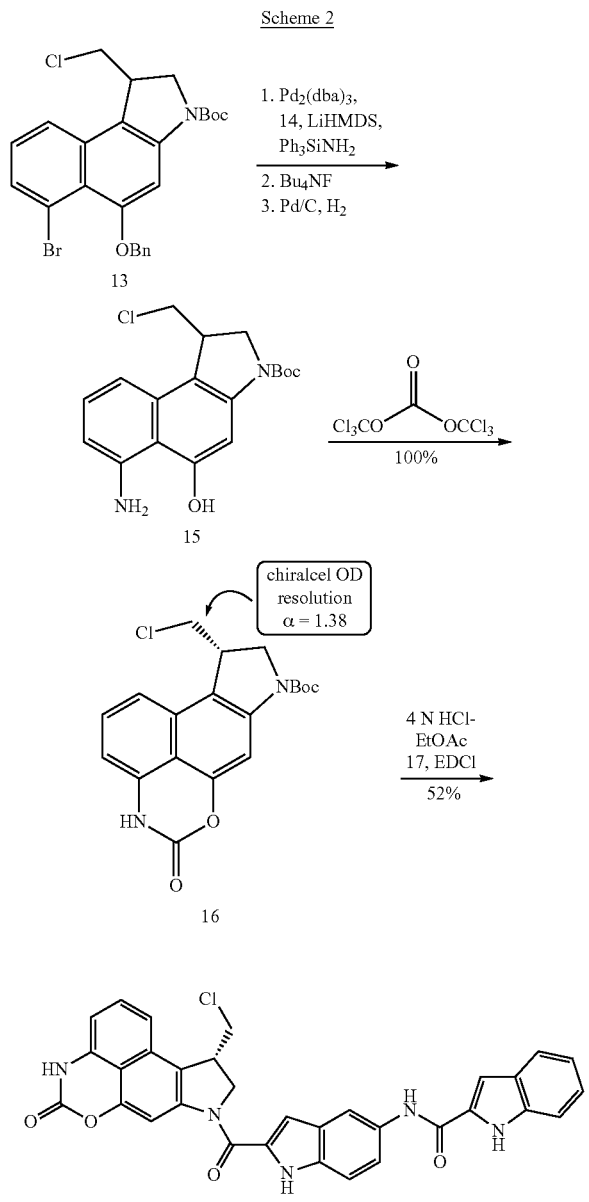

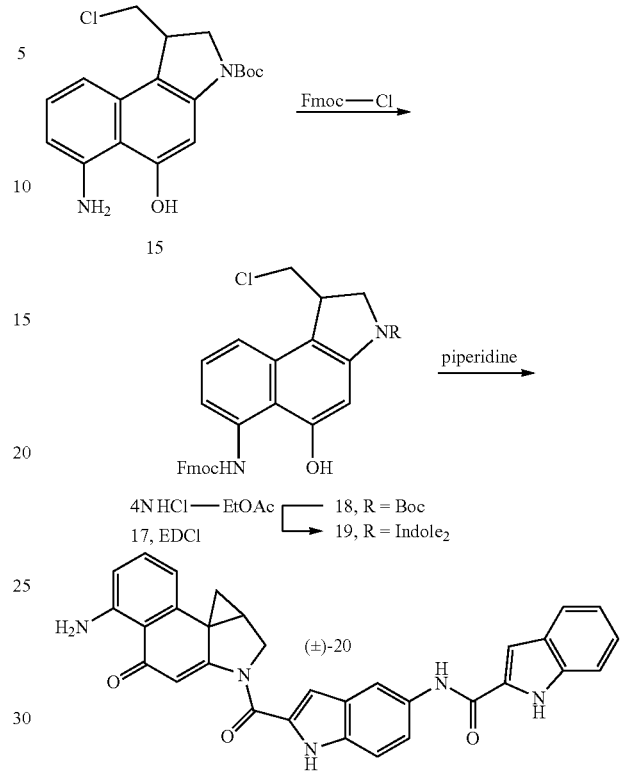

Stability of the Cyclic Carbamate Prodrug

In order to determine the ability of the free drug to be released under physiological conditions, the chemical reactivity of N-Boc-prodrug 16 was assessed under a variety of acidic, basic, and nucleophilic conditions. The cyclic carbamate of 16 proved robust to hydrolysis under acidic conditions (1:1 TFA:$CH_2Cl_2$, 4 N HCl in EtOAc) and was stable over a period of 48 h at 23° C., although the Boc protecting group was readily cleaved under such conditions. As shown in Table 1, 16 was also stable to organic bases in aprotic solvents (entries 1-3), but the cyclic carbamate was slowly hydrolyzed in the presence of $NaHCO_3$ in protic solvents in a reaction that proceeded at a greater rate as the polarity of the solution increased (entries 3-6). Compound 16 was found to be completely stable in the presence of the nucleophiles BnSH and BnOH (100 equiv) in MeOH and THF at 23° C. for 48 h, and was stable to $BnNH_2$ in THF, but was rapidly cleaved with $BnNH_2$ (100 equiv) in MeOH in 24 h.

TABLE 1

N-Boc prodrug 16 stability under basic conditions.

| Entry | Solvent | Base[a] | 2 h[b] | 24 h[b] | 48 h[b] |
|---|---|---|---|---|---|
| 1 | $CH_2Cl_2$ | $Et_3N$ | stable | stable | stable |
| 2 | $CH_2Cl_2$ | DMAP | stable | stable | 12% |
| 3 | THF | $NHCO_3$ | stable | stable | 7% |
| 4 | THF:$H_2O$ (1:1) | $NHCO_3$ | <4% | 4% | 9% |
| 5 | DMF:$H_2O$ (1:1) | $NHCO_3$ | 7% | 12% | 19% |
| 6 | MeOH | $NHCO_3$ | 18% | 74% | 100% |

[a]excess base (>100 equiv) used;
[b]percent of 16 hydrolyzed as determined by LCMS analysis at 254 nm absorption; all reactions were run at 23° C.

The parent compound of 6 was prepared as shown in Scheme 3 through a four step sequence. The aniline of intermediate 15 was differentially protected as a Fmoc carbamate. Subsequent Boc deprotection and coupling with carboxylic acid 17 gave 19, which was Fmoc deprotected and cyclized upon treatment with piperidine to provide the parent compound 20 as a racemic mixture.

The stability of the full prodrug 6 was examined in pH 7.0 phosphate buffer ($t_{1/2}$>4 weeks, no cleavage observed) and in human plasma ($t_{1/2}$>48 h, 5% free drug release) indicating that the cyclic carbamate is remarkably stable under both conditions. By contrast, the open chain carbamates explored in earlier studies leading to KW-2189 and carzelesin were designed for much more rapid release (1-20 h). We also found that 6 is incapable of alkylating DNA in cell-free systems[23], indicating that any in vitro cytotoxic activity or in vivo antitumor activity of 16 or 6 is due to release of the free drug.

Biological Methods and Prodrug Properties

In Vitro Cytotoxic Activity. Both (+)- and ent-(−)-6 and their N-Boc precursors 16 were tested for cell growth inhibition in a cytotoxic assay with the L1210 murine leukemia cell line. The natural enantiomer of the prodrug (+)-6 was found to be approximately 200-fold less potent ($IC_{50}$ of 6.6 nM) than the free drug seco-CBI-indole$_2$ 4 ($IC_{50}$ of 30 pM) and 6-fold more potent that its unnatural enantiomer. The racemic parent drug (±)-20 was found to have an $IC_{50}$ of 210 pM, suggesting that the active enantiomer is approximately 3-4 fold less active than 4, and indicating that the prodrug (+)-6 is 30-70 fold less potent than the parent drug 20. Consistent with expectations, the full prodrug 6 proved to be 100 to 1000 times more potent than its N-Boc precursor 16, which in turn is 50-100 fold less active than N-Boc-CBI (natural enantiomer $IC_{50}$=80 nM).[9] These data are consistent with the remarkable stability of the prodrug to chemical hydrolysis conditions, pH 7 phosphate buffer, and in human plasma, and its ineffective in vitro DNA alkylation reaction[21], indicating that the release of free drug is similarly slow even under the conditions of an in vitro cellular assay as well. Despite the lower potency relative to the free drug 4 and the racemic parent compound 20, it is notable that the cyclic carbamate prodrug (+)-6 now displays an in vitro cellular potency ($IC_{50}$=1-10 nM) on par with most clinically used antitumor drugs.

TABLE 2

In vitro cytotoxic activity.

| Compd | $IC_{50}$ L1210 | |
|---|---|---|
| | natural (nM) | unnatural (nM) |
| 1, duocarmycin SA | 0.010 | 0.100 |
| 2, CC-1065 | 0.020 | 0.020 |
| 4, CBI-indole$_2$ | 0.030 | 0.900 |
| 16 | 4900 | 5800 |
| 6 | 6.6 | 40 |
| (±)-20 | | 0.210 |

In Vivo Antitumor Activity.

Even though results of the in vitro cellular assay showed that (+)-6 is substantially less potent than its parent drug, the slow release of the compound could prove to be advantageous in vivo due to the inherent potency and toxicity of the parent compound. Therefore, the in vivo antitumor activity of (+)-6 was assessed alongside seco-CBI-indole$_2$ (4) in an antitumor model consisting of L1210 murine leukemia cells implanted ip into DBA/2J mice which has been used historically as an initial antitumor model for comparisons in this class.[11,12,14,15] A dose range of 300 to 9000 μg/kg for prodrug (+)-6 (scaled to its in vitro cytotoxic activity $IC_{50}$) and 60 to 500 μg/kg for seco-CBI-indole$_2$ (4) and a dosing schedule (administered three times ip on days 1, 5, and 9) for both compounds was employed. A subtle, but additional important empirical observation made in the studies is that the prodrug administration is tolerated at the injection sites of the animals much better than the free drug.

TABLE 3

In vivo antitumor activity (L1210, ip).

(+)-6

| Compd | Dose μg/kg[a] | MSP days[b] | T/C[c] | Surviving Mice[d] |
|---|---|---|---|---|
| none | 0 | 17.6 | 100 | 0/10 |
| 4 | 60 | >34.7 | >197 | 1/10 |
| 4 | 100 | 6.4 | 36 | 0/10 |
| 4 | 250 | 3.7 | 21 | 0/10 |
| 4 | 500 | 3.0 | 17 | 0/10 |
| 6 | 300 | 24.7 | 140 | 0/10 |
| 6 | 1000 | >48.5 | >275 | 1/10 |
| 6 | 3000 | >55.3 | >310 | 1/10 |
| 6 | 9000 | >172.6 | >980 | 5/10 |

[a]Dose (μg/kg wt. of animal) administered i.p. on days 1, 5, and 9.
[b]MSP = Mean Survival Period (days).
[c]T/C = Treated/Control (MSP) x 100.
[d]No. of live animals after 250 days (terminated).

The optimal does range for 4 was previously established (60-100 μg/kg) and was extended for the study herein to highlight its narrow therapeutic window versus the potential behavior of prodrug (+)-6. As anticipated, (+)-CBI-indole$_2$ (4) proved toxic at doses of 100-500 μg/kg leading to premature death of the animals and productive antitumor activity was observed only at the dose of 60 μg/kg (T/C=197), albeit producing only 1/10 long term (250 days) survivors in this extended study (FIG. 6). By contrast, the prodrug (+)-6 exhibited productive antitumor activity over the entire and much larger dose range examined (30-fold range). The most efficacious activity was observed at the highest dose of 9000 μg/kg, producing 5/10 long term cures (>250 days, T/C>980) and indicating that even higher doses may be not only tolerable, but potentially even more efficacious. This highest dose represents one that is 150 times greater than the optimal dose observed with (+)-4, in line with the 100-200 fold differences in their cytotoxic potencies. In addition the dose range of over which (+)-6 exhibited productive activity was much larger, the in vivo antitumor activity was more efficacious (T/C>980), and long term cures (5/10>250 day survivors) were observed even without an effort at dosing optimization.

TABLE 4

Imino and Thio Carbamate Analogs of the Invention

[Structure of compound with Cl, HN, X, O, N, H, NH groups shown]

(+)-6, X = O
(+)-24, X = NH
(+)-25, X = S
(+)-26, X = SCH$_3$
(+)-27, X = S(CH$_2$)$_3$CO$_2$Et
(+)-29, X = S(CH$_2$)$_2$NPhth In vitro

| Compd | IC$_{50}$ L1210 | |
|---|---|---|
|  | natural (nM) | unnatural (nM) |
| 1, duocarmycin SA | 0.010 | 0.100 |
| 2, CC-1065 | 0.020 | 0.020 |
| CBI-indole$_2$ | 0.030 | 0.900 |
| (+)-6 | 6.6 | 40 |
| (+)-24 | 0.500 | 64 |
| (+)-25 | 0.290 | 62 |
| (+)-26 | 6.6 | 578 |
| (+)-27 | 7.2 | N/A |
| (+)-29 | 83.6 | N/A |

Stability

| | t$_{1/2}$ | | | |
|---|---|---|---|---|
| Conditions | N-Boc-2 | (+)-6 | N-Boc— | (+)-7 |
| mouse plasma | | 12 h | | >2 h |
| pH 7.0 phosphate buffer | | >7 d | | 5 d |
| TFA/CH$_2$Cl$_2$ | >48 h | | 72 h | 40 h |
| DMAP/THF | 48 h | | 12 h | |
| NaHCO$_3$/THF | >72 h | | 40 h | |
| NaHCO$_3$/MeOH | >72 h | | 2 h | |

A novel heterocyclic carbamate prodrug 6 of (+)-CBI-indole$_2$, which can be released via hydrolysis, was synthesized and evaluated for its in vitro cytotoxic activity and in vivo antitumor activity. Compared to its open chain counterparts explored in earlier studies, the cyclic carbamate prodrug was found to be remarkably stable to chemical hydrolysis conditions as well as in pH 7.0 phosphate buffer and human plasma. Accordingly, 6 was less potent in vitro and in vivo compared to the parent drug 4, but was found to be substantially safer and more efficacious in vivo, being superior in extending life expectancy of tumor-bearing animals even at 150-fold higher doses. Notable elements of the cyclic carbamate prodrug behavior include not only its hydrolysis liberation of the free drug that releases no residual byproduct (CO$_2$), but also its remarkable stability relative to its acyclic counterparts explored in early studies. This results in an apparent slow, sustained release of free drug that permits the safer and more efficacious use of larger doses of drug (as much as 150-fold), effectively taming the extraordinary potency of this class of antitumor drugs.

In various embodiments, the invention provides prodrugs comprising analogs of cyclic carbamates, e.g., imino analogs (compound 24 of Table 4), and thioxo analogs (compound 25 of Table 4). The invention also provides S-alkylthio analogs (compounds 26, 27, and 29 of table 4), where a double bond is present to the carbamate nitrogen atom and the hydrogen atom is absent. In Table 4, natural and unnatural refer to the stereochemical configuration at the chiral carbon atom; natural being the (S)-enantiomer, and unnatural being the (R)-enantiomer. As can be seen, the natural enantiomer of all of compounds 24, 25, 26, 27 possess 1210 IC$_{50}$ values in the nanomolar range, and compound 29 has an IC50 value under 100 nM. In contrast, the unnatural (R)-enantiomers, determined for compounds 24-26 are about two orders of magnitude less potent in this bioassay. This parallels the observation for the cyclic carbamate 6, except for carbamate 6 the natural (S)-enantiomer is about one order of magnitude more potent.

General Methods

Reagents and solvents were purchased reagent-grade and used without further purification. Pooled human plasma, with sodium citrate as an anticoagulant, was purchased from Innovative Research and stored at −20° C. THF was freshly distilled from sodium benzophenone ketyl. t-BuOH was freshly distilled from calcium hydride. All reactions were performed in oven-dried glassware under an Ar atmosphere. Evaporation and concentration in vacuo was performed at 20° C. TLC was conducted using precoated. SiO$_2$ 60 F254 glass plates from EMD with visualization by UV light (254 or 366 nm). Chiral phase HPLC was performed using a Shimadzu HPLC on a semi-preparative Diacel ChiralCel OD column (0.46 cm×25 cm) with a flow rate of 7 mL/min and with UV detection at λ=254 nm. Optical rotations were determined on a Rudolf Research Analytical Autopol III Automatic Polarimeter (λ=589 nm, 25° C.). NMR ($^1$H or $^{13}$C) were recorded on Bruker DRX-500 and DRX-600 NMP spectrophotometers at 298K. Residual solvent peaks were used as an internal reference. Coupling constants (J) (H,H) are given in Hz. Coupling patterns are designated as singlet (s), doublet (d), triplet (t), quadruplet (q), multiplet (m), or broad singlet (br). IR spectra were recorded on a Thermo Scientific Nicolet 380 FT-IR spectrophotometer and measured neat. High resolution mass spectral data were acquired on an Agilent Technologies high resolution LC/MSD-TOF, and the detected masses are given as m/z with m representing the molecular ion. The purity of each tested compound (>95%) was determined on an Agilent 1100 LC/MS instrument using a ZORBAX SB-C18 column (3.5 mm, 4.6 mm×50 mm, with a flow rate of 0.75 mL/min and detection at 220 and 254 nm) with a 10-98% acetonitrile/water/0.1% formic acid gradient.

Ethyl 5-Bromo-4-hydroxy-2-naphthoate (7)

A solution of potassium tert-butoxide (20.0 g, 0.78 mol) at 55° C. in t-BuOH (249 mL) was treated with a premixed solution of diethyl succinate (40.4 mL, 0.243 mol) and 3-bromobenzaldehyde (18.9 mL, 0.162 mol) dropwise. Upon completion of the addition, the reaction mixture was warmed to 85° C. and stirred for 2 h. After 2 h, the reaction mixture was cooled to 25° C. The reaction mixture was acidified to pH<4 with 2 N aqueous HCl and concentrated. The aqueous suspension was then extracted with ethyl acetate (3×). The organic layers were combined and washed with saturated aqueous NaHCO$_3$ (5×). The basic aqueous washes were combined and reacidified with 2 N aqueous HCl to pH 1. Finally, the aqueous phase was extracted with ethyl acetate (3×). The organic layers were combined, dried over Na$_2$SO$_4$, and concentrated under reduced pressure, which afforded the desired half ester (39.1 g, 77%) as an orange oil. The half ester (39.1 g, 0.124 mol) was dissolved in acetic anhydride (178 mL) and NaOAc (18.7 g, 0.137 mol) was added. The reaction mixture was warmed to 140° C. and stirred for 6 h. Upon completion, the reaction mixture was cooled to 25° C. and poured into H$_2$O. The aqueous layer was extracted with ethyl acetate (3×). The organic layers were combined, dried over Na$_2$SO$_4$, and concentrated under reduced pressure. The residue was dissolved in anhydrous ethanol (620 mL). K$_2$CO$_3$ (104 g, 0.624 mol) was added, and the reaction mixture was warmed at 80° C. for 1 h. The reaction mixture was cooled and acidified to pH 1 with 2 N aqueous HCl. The ethanol was removed under reduced pressure and the aqueous suspension was extracted with ethyl acetate (3×). The organic extracts were combined, dried over Na$_2$SO$_4$, and concentrated under reduced pressure. Flash chromatography (SiO$_2$, 16×30 cm, 0-15% EtOAc/hexanes gradient elution) provided 7 (5.4 g, 15% over 3 steps) as a yellow solid and its 7-bromo isomer (12.4 g, 34% over 3 steps). $^1$H NMR (CDCl$_3$, 500 MHz) δ 8.16 (s, 1H), 8.07 (s, 1H), 7.89 (d, J=6.5 Hz, 1H), 7.73 (d, J=6.5 Hz, 1H), 7.63 (s, 1H), 7.29 (t, J=10 Hz, 1H), 4.43 (q, J=6.0 Hz, 2H) 1.44 (t, J=6.0 Hz, 3H). $^{13}$C NMR (CDCl$_3$, 125 MHz) δ 165.9, 152.7, 136.3, 133.6, 130.6, 129.2, 126.7, 123.6, 122.7, 115.2, 112.3, 61.3, 14.3. IR (film) ν$_{max}$ 3367, 2979, 1690, 1227 cm$^{-1}$. ESI-TOF HRMS m/z 294.9959 (M+H$^+$, C$_{13}$H$_{11}$BrO$_3$ requires 294.9964).

Ethyl 4-(Benzyloxy)-5-bromo-2-naphthoate (8)

Naphthol 7 (3.20 g, 11.0 mmol) was dissolved in anhydrous DMF (78 mL). K$_2$CO$_3$ (3.05 g, 22.0 mmol), benzyl bromide (1.59 mL, 13.2 mmol), and Bu$_4$NI (163 mg, 0.440 mmol) were added. The solution was stirred at 25° C. for 16 h. The reaction mixture was poured into H$_2$O and extracted with ethyl acetate (3×). The organic extracts were combined, dried over Na$_2$SO$_4$, and concentrated under reduced pressure. The solid was recrystallized with 5% EtOAc/hexanes and the mother liquor was further purified by flash chromatography (SiO$_2$, 6×15 cm, 10-20% EtOAc/hexanes gradient elution) affording additional 8 (3.30 g combined, 77%) as a brown crystalline solid. $^1$H NMR (CDCl$_3$ 500 MHz) δ 8.17 (s, 1H), 7.87 (d, J=7.5 Hz, 1H), 7.85 (d, J=8.0 Hz, 1H), 7.61 (d, J=7.5 Hz, 2H), 7.57 (s, 1H), 7.40 (t, J=7.5 Hz, 2H), 7.35-7.32 (m, 1H), 7.29 (t, J=7.5 Hz, 1H), 5.30 (s, 2H), 4.43 (q, J=7.0 Hz, 2H), 1.44 (t, J=7.0 Hz, 3H). $^{13}$C NMR (CDCl$_3$, 125 MHz) δ 166.0, 154.5, 136.1, 136.0, 135.0, 129.3, 128.3, 128.0 (2C), 127.8, 126.8, 125.8, 124.1, 116.7, 106.9, 71.2, 61.1. IR (film) ν$_{max}$ 2980, 1712, 1413, 1236 cm$^{-1}$. ESI-TOF HRMS m/z 385.0433 (M+H$^+$, C$_{20}$H$_{17}$BrO$_3$ requires 385.0434).

4-(Benzyloxy)-5-bromo-2-naphthoic Acid (9)

Ester 8 (2.29 g, 5.94 mmol) was dissolved in a 3:1:1 mixture of THF:CH$_3$OH:H$_2$O (0.1 M). LiOH—H$_2$O was added and the reaction mixture was stirred at 25° C. for 24 h. Upon completion, the reaction mixture was acidified to pH 1 with the addition of 10% aqueous HCl. A precipitate formed during the acidification and it was collected by vacuum filtration. The remaining aqueous layer was then extracted with ethyl acetate (3×). The organic extracts were combined, dried over Na$_2$SO$_4$, and concentrated under reduced pressure. The filtered and extracted products were combined to give 9 (2.09 g, 100%) as a pale yellow solid. $^1$H NMR (DMSO-d$_6$, 500 MHz) δ 8.23 (s, 1H), 8.10 (d, J=6.0 Hz, 1H), 7.91 (d, J=6.5 Hz, 1H), 7.61 (d, J=7.0 Hz, 2H), 7.55 (s, 1H), 7.43-7.39 (m, 3H), 7.33 (t, J=7.0 Hz, 1H), 5.35 (s, 2H). $^{13}$C NMR (DMSO-d$_6$, 125 MHz) δ 166.7, 153.8, 136.2, 135.9, 135.0, 129.8, 128.8, 128.2, 127.8, 127.7, 127.5, 124.7, 123.8, 115.5, 107.0, 70.4. IR (film) ν$_{max}$ 3368, 2969, 1680 cm$^{-1}$. ESI-TOF HRMS m/z 357.0125 (M+H$^+$, C$_{18}$H$_{13}$BrO$_3$ requires 357.0121).

tert-Butyl-(4-(benzyloxy)-5-bromonaphthalen-2-yl) carbamate (10)

Carboxylic acid 9 (950 mg, 2.66 mmol) was dissolved in freshly distilled t-BuOH (0.01 M) over 4 Å molecular sieves. Et$_3$N (467 μL, 3.35 mmol) and diphenylphosphoryl azide (602 μL, 2.79 mmol) were added. The reaction mixture was warmed to 85° C. under Ar and stirred for 14 h. Upon completion, the mixture was filtered through cotton to remove the molecular sieves and concentrated under reduced pressure. The residue was diluted with 10% aqueous HCl and extracted with EtOAc (3×). The organic extracts were combined and washed with H$_2$O (2×) and saturated aqueous NaCl. The organic phase was dried over Na$_2$SO$_4$, and concentrated under reduced pressure. Flash chromatography (SiO$_2$, 5×12 cm, 5% EtOAc/hexanes elution) provided 10 (1.02 g, 89%) as a tan solid. $^1$H NMR (CDCl$_3$, 600 MHz) δ 7.62 (m, 2H), 7.58 (d, J=7.8 Hz, 2H), 7.49 (s, 1H), 7.39 (t, J=7.2 Hz, 2H), 7.33 (t, J=6.0 Hz, 1H), 7.16 (t, J=7.8 Hz, 1H), 7.03 (s, 1H), 6.58 (s, 1H), 5.22 (s, 2H), 1.54 (s, 9H). $^{13}$C NMR (CDCl$_3$, 150 MHz) δ 155.2, 152.5, 137.6, 136.4, 136.3, 131.3, 130.0, 128.4, 127.9, 127.3, 126.9, 120.4, 120.2, 120.1, 116.6, 107.8, 101.8, 71.4, 28.3. IR (film) ν$_{max}$ 3325, 2977, 1702, 1156 cm$^{-1}$. ESI-TOF HRMS m/z 428.0856 (M+H$^+$, C$_{22}$H$_{22}$BrNO$_3$ requires 428.0856).

tert-Butyl-(4-(benzyloxy)-5-bromo-1-iodonaphthalen-2-yl)carbamate (11)

Carbamate 10 (1.20 g, 2.80 mmol) was dissolved in freshly distilled THF (0.17 M) under Ar and in the absence of light, and TsOH□H$_2$O (53 mg, 0.28 mmol) and N-iodosuccinamide (753 mg, 3.30 mmol) were added. The reaction mixture was allowed to stir at 25° C. for 2 h. After 2 h, the reaction was quenched with the addition saturated aqueous NaHCO$_3$ and diluted with ethyl acetate. The organic layer was washed with saturated aqueous NaCl, dried over Na$_2$SO$_4$, and concentrated under reduced pressure. Flash chromatography (SiO$_2$, 5×16 cm, 5% EtOAc/hexanes elution) provided 11 (1.47 g, 94%) as an orange solid. $^1$H NMR (CDCl$_3$, 500 MHz) δ 8.16 (s, 1H), 8.09 (d, J=8.0 Hz, 1H), 7.70 (d, J=7.5 Hz, 1H), 7.62 (d, J=7.0 Hz, 2H), 7.39 (t, J=7.2 Hz, 2H), 7.34 (d, J=7.0 Hz, 1H), 7.32 (s, 1H), 7.25-7.22 (m, 2H), 5.28 (s, 2H), 1.58 (s, 9H). $^{13}$C NMR (CDCl$_3$, 125 MHz) δ 155.8, 152.4, 139.0, 136.7, 135.9, 132.2, 131.9, 130.0, 128.5, 128.3, 128.0, 127.9, 121.4, 120.2, 120.1, 117.0, 101.9, 81.3, 71.3, 28.3. IR (film) ν$_{max}$ 3378, 2978, 1730, 1225, 1145 cm$^{-1}$. ESI-TOF HRMS m/z 553.9820 (M+H$^+$, C$_{22}$H$_{21}$BrINO$_3$ requires 553.9822).

tert-Butyl-(4-(benzyloxy)-5-bromo-1-iodonaphthalen-2-yl)-(3-chloroallyl)carbamate (12)

Compound 11 (1.65 g, 2.99 mmol) and Bu$_4$NI (55 mg, 0.15 mmol) were dissolved in anhydrous DMF (0.16 M) and the solution was cooled to 0° C. Once cooled, 60% NaH in mineral oil (239 mg, 5.98 mmol) was added and the reaction mixture was allowed to stir at 0° C. for 30 min. 1,3-Dichloropropene (0.84 mL, 8.97 mmol) was added dropwise and the solution was warmed to room temperature. After 1 h, the reaction mixture was quenched with the addition of saturated aqueous NH$_4$Cl and diluted with ethyl acetate. The organic layer was washed with H$_2$O, saturated aqueous NaCl, dried over Na$_2$SO$_4$, and concentrated under reduced pressure. Flash chromatography (SiO$_2$, 5×8 cm, 10% EtOAc/hexanes elution) provided an E/Z mixture of alkene 12 (1.818 g, 96%) as a yellow foam. $^1$H NMR (acetone-d$_6$, 600 MHz) δ 8.35 (m, 2H), 7.92 (d, J=7.2 Hz, 2H), 7.61 (br, 4H) 7.45 (t, J=8.4 Hz, 2H), 7.42-7.40 (m, 4H), 7.35-7.33 (m, 2H), 7.18 (d, J=18.0 Hz, 2H), 6.21-6.08 (m, 3H), 5.39 (s, 4H), 4.60 (dd, J=18.9, 5.4 Hz, 1H), 4.42 (dd, J=15.0, 7.2 Hz, 1H), 4.27 (dd, J=15.6, 6.6 Hz, 1H), 3.99 (dd, J=14.1, 6.6 Hz, 1H), 1.55 (br, 4H), 1.28 (br, 14H). $^{13}$C NMR (acetone-d$_6$, 150 MHz) δ 157.28, 157.27, 154.8, 154.6, 145.9, 145.8, 139.2, 139.1, 138.2, 138.1, 136.13, 136.12, 135.4 (2C), 130.9, 130.2, 130.1, 129.9, 129.86, 129.81, 129.7, 129.4, 126.2, 125.4, 123.2, 122.2, 118.2, 112.4, 112.3, 98.0, 97.2, 82.2, 81.8, 72.8, 72.6, 50.6, 47.3, 29.3. IR (film) ν$_{max}$ 2974, 2928, 1697, 1156, 749 cm$^{-1}$. ESI-TOF HRMS m/z 627.9750 (M+H$^+$, C$_{25}$H$_{24}$BrClNO$_3$ requires 627.9746).

tert-Butyl 1,2-Dihydro-5-(benzyloxy)-6-bromo-1-(chloromethyl)-1H-benzo[e]indole-3(2H)-carboxylate (13)

Alkene 12 (1.81 g, 2.89 mmol) and AIBN (140 mg, 0.86 mmol) were dissolved in benzene (0.05 M). Freshly prepared Bu$_3$SnH (701 μL, 2.60 mmol) was added and the system was purged of oxygen using Ar and the freeze/pump/thaw method. The reaction mixture was warmed to 80° C. for 12 h. Upon completion, the reaction mixture was concentrated under reduced pressure and purified by flash chromatography (10% w/w KF fused SiO$_2$, 5×16 cm, 0-10% EtOAc/hexanes gradient elution) to provide 13 (1.32 g, 90%) as a white solid. $^1$H NMR (acetone-d$_6$, 600 MHz) δ 7.98 (br, 1H), 7.81 (d, J=8.4 Hz, 1H), 7.65-7.63 (m, 3H), 7.41 (t, J=7.2 Hz, 2H), 7.35-7.30 (m, 2H), 5.31 (s, 2H), 4.21-4.16 (m, 2H), 4.12-4.09 (m, 1H), 3.96 (dd, J=11.1, 3.0 Hz, 1H), 3.71 (dd, J=8.4, 11.4 Hz, 1H), 1.58 (s, 9H). $^{13}$C NMR (acetone-d$_6$, 150 MHz) δ 157.8, 153.8, 144.3, 138.4, 135.0, 132.6, 130.1 129.7, 129.4, 124.9, 124.3, 121.6, 119.4, 117.2, 100.7, 82.4, 72.8, 54.4, 48.6, 43.1, 29.5. IR (film) ν$_{max}$ 2926, 1692, 1330, 1135, 752 cm$^{-1}$. ESI-TOF HRMS m/z 502.0772 (M+H$^+$, C$_{25}$H$_{25}$BrClNO$_3$ requires 502.0779).

tert-Butyl 1,2-Dihydro-6-amino-1-(chloromethyl)-5-hydroxy-1H-benzo[e]indole-3(2H)-carboxylate (15)

An oven-dried microwave vial was charged with Pd$_2$(dba)$_3$ (10.9 mg, 11 μmol), 2-dicyclohexylphosphinobiphenyl (14, 8.3 mg, 0.023 mmol), and (C$_6$H$_5$)$_3$SiNH$_2$ (72.1 mg, 0.261 mmol). The vial was evacuated and filled with Ar. Compound 13 (120 mg, 0.238 mmol) was added and the vial was evacuated again. Toluene (2.3 mL) was added and the vessel was purged with Ar. Finally, LiHMDS (0.29 mL, 1 M in THF) was added and the vessel was sealed. The reaction was submerged in a 100° C. oil bath for 24 h. After 24 h, the reaction mixture was cooled to room temperature, diluted with diethyl ether, filtered through a plug of Celite, and concentrated. The residue was dissolved in THF (15 mL) and cooled to 0° C. Bu$_4$NF (0.36 mL, 1 M in THF) was added dropwise. The reaction mixture was allowed to stir for 30 min before being quenched with the addition of saturated aqueous NH$_4$Cl and diluted with ethyl acetate. The organic layer was washed with saturated aqueous NaCl, dried over Na$_8$SO$_4$, and concentrated. The residue was purified by flash chromatography (SiO$_2$, 4×8 cm, 5-10% EtOAc/hexanes gradient elution). The product was carried on to the next reaction mixture without characterization due to co-elution of triphenyl byproduct. The amine (104 mg theoretical, 0.238 mmol) was dissolved in anhydrous CH$_3$OH (6 mL) under Ar. 10% Pd/C (29 mg, 0.024 mmol) was added and the atmosphere was exchanged with H$_2$. The reaction mixture was allowed to stir at 25° C. for 5 h. The reaction mixture was diluted with diethyl ether, filtered through Celite, and concentrated under reduced pressure. Flash chromatography (SiO$_2$, 3×8 cm, 50-70% Et$_2$O/hexanes gradient elution) provided 15 (56 mg, 67% over 3 steps) as a tan solid. $^1$H NMR (acetone-d$_6$, 600 MHz) δ 7.48 (br, 1H), 7.12 (t, J=7.8 Hz, 1H), 6.84 (d, J=7.8 Hz, 1H), 6.44 (d, J=6.6 Hz, 1H), 4.13-4.05 (m, 2H), 3.92-3.87 (m, 2H), 3.55 (t, J=10.8 Hz, 1H), 1.54 (s, 9H). $^{13}$C NMR (acetone-d$_6$, 150 MHz) δ 158.6, 153.7, 148.8, 134.8, 130.0, 126.8, 115.3, 112.5, 111.4, 108.7, 99.6, 81.7, 54.1, 48.3, 43.4, 29.3. IR (film) ν$_{max}$ 3391, 2974, 1706, 1583, 1406, 1142 cm$^{-1}$. ESI-TOF HRMS m/z 349.1323 (M+H$^+$, C$_{18}$H$_{21}$ClN$_2$O$_3$ requires 349.1313).

tert-Butyl 10-(Chloromethyl)-5-oxo-9,10-dihydro-4H-pyrrolo[3',2':5,6]naphtho[1,8-de][1,3]oxazine-8(5H)-carboxylate (16)

Naphthol 15 (56 mg, 0.160 mmol) and triphosgene (47 mg, 0.160 mmol) were dissolved in toluene (3.2 mL) at 25° C. The reaction mixture was stirred for 1 h before being diluted with H$_2$O and ethyl acetate. The organic layer was washed with saturated aqueous NaCl, dried over Na$_2$SO$_4$, and concentrated under reduced pressure. Flash chromatography (SiO$_2$, 2×6 cm, 20-50% EtOAc/hexanes gradient elution) provided 16 (60 mg, 100%) as a yellow solid. $^1$H NMR (acetone-d$_6$, 600 MHz) δ 9.86 (s, 1H), 7.66 (br, 1H), 7.37 (t, J=8.4 Hz, 1H), 7.32 (d, J=8.4 Hz, 1H), 6.66 (d, J=7.8 Hz, 1H), 4.19-4.18 (m, 2H), 4.07-4.05 (m, 1H), 3.98 (dd, J=11.1, 3.6 Hz, 1H), 3.77 (dd, J=8.2, 11.4 Hz, 1H), 1.58 (s, 9H). $^{13}$C NMR (acetone-d$_6$, 150 MHz) δ 178.5, 153.7, 152.8, 148.37, 148.31, 146.1, 137.0, 136.9, 131.8, 131.2, 118.8, 116.8, 110.0, 105.5, 100.3, 82.7, 54.5, 48.5, 42.5, 29.4. IR (film) ν$_{max}$ 2924, 1701, 1606, 1405, 1332, 1140 cm$^{-1}$. ESI-TOF HRMS m/z 375.1105 (M+H$^+$, C$_{19}$H$_{19}$ClN$_2$O$_4$ requires 375.1106).

The enantiomers were resolved on a semi-preparative Diacel chiralcel OD column (0.46 cm×25 cm) with 20% i-PrOH/hexanes elution; α=1.38.

(1S)-16: [α]$^{23}$$_D$ −31 (c 0.75, THF), natural enantiomer.
(1R)-16: [α]$^{23}$$_D$ +32 (c 0.80, THF), unnatural enantiomer.

N-(2-(10-(Chloromethyl)-5-oxo-5,8,9,10-tetrahydro-4H-pyrrolo[3',2':5,6]naphtho[1,8-de][1,3]oxazine-8-carbonyl)-1H-indol-5-yl)-1H-indole-2-carboxamide (6)

Compound 16 (7.5 mg, 0.020 mmol) was dissolved in 4 N HCl in EtOAc (0.5 mL) and the mixture was allowed to stir at room temperature for 25 min. The solvent was removed under a stream of nitrogen and the residue was redissolved in anhydrous DMF (0.4 mL). EDCI (11.4 mg, 0.06 mmol) and 17 (7.0 mg, 0.022 mmol) were added and the reaction mixture was allowed to stir at 25° C. for 24 h. The reaction mixture was quenched with the addition of H$_2$O and diluted with ethyl acetate. The organic phase was washed with 2 N aqueous HCl (3×), saturated aqueous NaHCO$_3$ (5×), and saturated aqueous NaCl. The organic extract was dried over Na$_2$SO$_4$ and concentrated under reduced pressure. The residue was purified by PTLC (SiO$_2$, 40% THF/toluene) to provide 6 (6.08 mg, 52%, typically 52-60%) as a tan solid. $^1$H NMR (DMSO-d$_6$, 600 MHz) δ 11.85 (s, 1H), 11.75 (s, 1H), 11.14 (br, 1H), 10.20 (s, 1H), 8.25 (s, 1H), 7.91 (s, 1H), 7.67 (d, J=8.4 Hz, 1H), 7.59 (dd, J=9.0, 1.8 Hz, 1H), 7.48 (t, J=9.0 Hz, 2H), 7.43 (m, 4H), 7.27 (s, 1H), 7.21 (t, J=7.8 Hz, 1H), 7.07 (t, J=7.8 Hz, 1H), 6.66 (dd, J=5.7, 3.0 Hz, 1H), 4.87 (t, J=10.2 Hz, 1H), 4.61 (dd, J=10.8, 2.4 Hz, 1H), 4.03-4.02 (m, 1H), 4.00-3.98 (m, 2H). $^{13}$C NMR (DMSO-d$_6$, 150 MHz) δ 160.2, 159.4, 149.8, 146.5, 143.4, 136.6, 134.8, 133.3, 131.8, 131.7, 130.7, 129.5, 129.1, 127.9, 127.03, 127.00, 126.9, 123.4, 121.5, 119.5, 119.4, 118.7, 115.3, 112.8, 112.29, 112.21, 108.7, 106.1, 104.4, 103.3, 99.8, 54.7, 47.2, 40.8. IR (film) $v_{max}$ 3255, 1731, 1603, 1514, 1400, 1232, 794, 733 cm$^{-1}$. ESI-TOF HRMS m/z 576.1431 (M+H$^+$, $C_{32}H_{22}ClN_5O_4$ requires 576.1433).

(1S)-6: $[\alpha]^{23}_D$+18.4 (c 0.21, THF), natural enantiomer.
(1R)-6: $[\alpha]^{23}_D$-18.5 (c 0.24, THF), unnatural enantiomer.

N-(2-(5-Amino-4-oxo-1,2,9,9a-tetrahydrocyclopropa[c]benzo[e]indole-2-carbonyl)-1H-indol-5-yl)-1H-indole-2-carboxamide (20)

Intermediate 15 (10 mg, 0.028 mmol) was suspended in H$_2$O (0.4 mL) and cooled to 0° C. Fmoc-Cl (9.6 mg, 0.037 mmol) in dioxane (0.2 mL) was added and the reaction mixture was allowed to slowly warm to room temperature over 17 h. The reaction mixture was diluted with H$_2$O and extracted with EtOAc (2×). The organic layers were combined, dried over Na$_2$SO$_4$, and concentrated under reduced pressure. The residue was dissolved in 4 N HCl in EtOAc (0.8 mL) and the mixture was allowed to stir at room temperature for 25 min. The solvent was removed under a stream of nitrogen and the residue was redissolved in anhydrous DMF (0.8 mL). EDCI (10.7 mg, 0.056 mmol) and 17 (10.7 mg, 0.34 mmol) were added and the reaction mixture was allowed to stir at 25° C. for 24 h. The reaction mixture was quenched with the addition of H$_2$O and diluted with EtOAc. The organic phase was washed with 2 N aqueous HCl (3×), saturated aqueous NaHCO$_3$ (5×), and saturated aqueous NaCl. The organic extract was dried over Na$_2$SO$_4$ and concentrated under reduced pressure. The crude residue was dissolved in DMF (0.8 mL) and piperidine (160 μL) was added. The reaction mixture was allowed to stir at room temperature for 1 h after which the solvent was removed under reduced pressure. The residue was purified by PTLC (SiO$_2$, 60% THF/toluene) to provide 20 (4.1 mg, 29% over 4 steps) as a yellow solid. $^1$H NMR (DMSO-d$_6$, 600 MHz) δ11.81 (s, 1H), 11.72 (s, 1H), 10.17 (s, 1H), 8.21 (s, 1H), 7.67 (d, J=7.8 Hz, 1H), 7.60 (d, J=9.0 Hz, 1H), 7.47 (d, J=9.0 Hz, 2H), 7.42 (s, 1H), 7.25 (s, 1H), 7.21 (t, J=7.8 Hz, 1H), 7.17 (t, J=8.4 Hz, 1H) 7.07 (t, J=7.8 Hz, 1H), 6.81 (s, 1H), 6.58 (d, J=8.4 Hz, 1H), 6.20 (d, J=7.2 Hz, 1H), 4.60-4.57 (m, 1H), 4.45 (d, J=10.2 Hz, 1H), 3.07 (m, 1H), 1.61 (t, J=4.8 Hz, 1H), 1.51-1.49 (m, 1H). $^{13}$C NMR (DMSO-d$_6$, 150 MHz) δ 188.8, 161.1, 159.2, 158.4, 150.5, 142.1, 136.4, 133.4, 132.4, 131.5, 131.4, 129.7, 126.7, 126.6, 123.2, 121.2, 119.6, 119.5, 113.6, 112.9, 112.6, 112.0, 110.5, 107.7, 106.8, 103.1, 63.1, 53.6, 32.4, 29.8, 24.1. ESI-TOF HRMS m/z 514.1872 (M+H$^+$, $C_{31}H_{23}N_5O_3$ requires 514.1874).

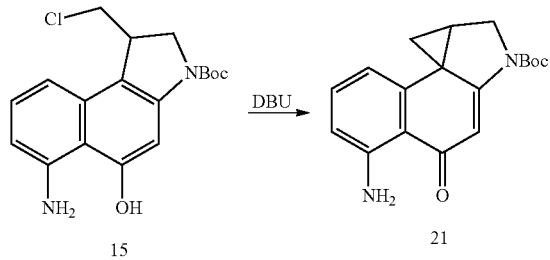

N-tert-Butyloxycarbonyl-5-amino-1,2,9,9a-tetrahydrocyclopropa[c]benzo[e]indole-4-one (N-Boc-ACBI, 21)

Compound 15 (4 mg, 11.4 μmol) in 0.2 mL of acetonitrile was treated with 1,8-diazabicyclo[5.4.0]undec-7-ene (DBU, 6 μL, 0.043 mmol). The reaction mixture was allowed to stir a room temperature for 90 min. After 90 min the solvent was evaporated under reduced pressure and the residue was purified by PTLC (SiO$_2$, 50% EtOAc/hexanes) to provide 21 (3.5 mg, 100% yield) as an orange oil. $^1$H NMR (acetone-d$_6$, 600 MHz) δ 7.25 (br, 1H), 7.12 (t, J=7.8 Hz, 1H), 6.59 (d, J=8.4 Hz, 1H), 6.12 (d, J=7.2 Hz, 1H), 4.00-3.94 (m, 2H), 2.85 (m, 1H), 1.53 (s, 9H), 1.45-1.40 (m, 2H). $^{13}$C NMR (acetone-d$_6$, 150 MHz) δ 191.0, 159.6, 153.1, 152.8, 144.3, 134.0, 116.3, 115.2, 109.9, 109.5, 85.5, 54.2, 35.0, 31.9, 29.0, 25.5. ESI-TOF HRMS m/z 313.1553 (M+H$^+$, $C_{18}H_{20}N_2O_3$ requires 313.1547).

Solvolysis of 21:

Compound 21 was dissolved in CH$_3$OH (1.5 mL). The CH$_3$OH solution was mixed with aqueous buffer (pH 2, 1.5 mL). The buffer contained 4:1:20 (v:v:v) 1.0 M citric acid, 0.2 M Na$_2$HPO$_4$, and H$_2$O, respectively. After mixing, the solvolysis solutions were stoppered and kept at 25° C. in the dark. The UV spectrum of the solutions was measured 3-4 times in the first two days and once a day for 2-4 weeks. The UV monitoring was continued until no further change was detectable. The long-wavelength absorption at 380 nm and short-wavelength absorption at 255 nm were monitored. The solvolysis rate constant and half-life were calculated from the data recorded at the short wavelength (255 nm) from the least square treatment of the slopes of plots of time versus ln [(A$_{Final}$-A$_{initial}$)/(A$_{final}$-A)].

pH 1 buffer: 10 M citric acid: 0.2 M Na$_2$HPO$_4$: H$_2$O (4:1:20)
$t_{1/2}$=8.52 h, k=1.5×10$^{-5}$ s$^{-1}$ pH 2 buffer: 1.0 M citric acid: 0.2 M Na$_2$HPO$_4$: H$_2$O (4:1:20)
$t_{1/2}$=40.3 h, k=5×10$^{-6}$ s$^{-1}$ Cyclic Carbamimidate and Carbamothioate Prodrugs

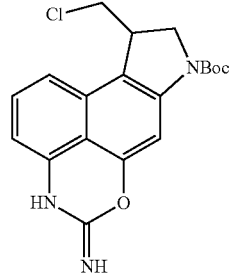 [SMILES: CC(C)(C)OC(=O)N1CC(CCl)c2c1cc1c3c(cccc23)NC(=N)O1]

tert-butyl 10-(chloromethyl)-5-imino-9,10-dihydro-4H-pyrrolo[3',2',5,6]naphtho[1,8-de][1,3]oxazine-8(5H)-carboxylate (22)

$^1$H NMR (THF-d$_8$, 600 MHz) δ 7.46 (br, 1H), 7.18 (t, J=7.8 Hz, 1H), 6.98 (d, J=8.4 Hz, 1H), 6.43 (d, J=7.2 Hz, 1H), 6.41 (br, 1H), 4.11-4.03 (m, 2H), 3.88-3.83 (m, 2H), 3.48 (t, J=10.2 Hz, 1H), 1.52 (s, 9H). $^{13}$C NMR (acetone-d$_6$, 150 MHz) δ 154.4, 152.8, 152.3, 143.7, 131.5, 131.1, 116.6, 114.2, 114.1, 114.0, 112.1, 96.9, 81.2, 53.6, 47.2, 42.7, 28.7. IR (film) $v_{max}$ 2924, 2360, 1704, 1591, 1331, 1257, 1072, 1017 cm$^{-1}$. ESI-TOF HRMS ink 374.1269 (M+H$^+$, $C_{19}H_{20}ClN_3O_3$ requires 374.1266).

The enantiomers were resolved on a semi-preparative Diacel chiralcel OD column (0.46 cm×25 cm) with 20% i-PrOH/hexanes elution; α=1.29.

(1S)-22: $[\alpha]^{23}_D$-17.9 (c 0.27, THF), natural enantiomer.
(1R)-22: $[\alpha]^{23}_D$+18.1 (c 0.26, THF), unnatural enantiomer.

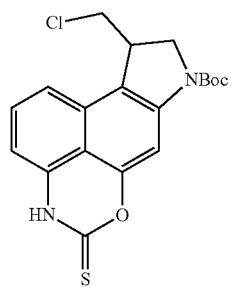 [SMILES: CC(C)(C)OC(=O)N1CC(CCl)c2c1cc1c3c(cccc23)NC(=S)O1]

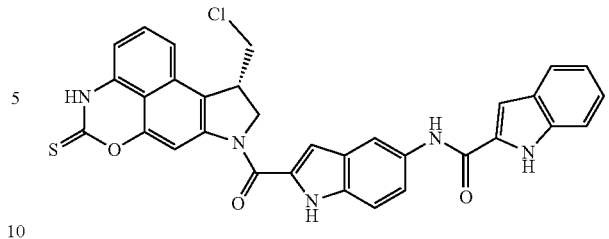

(S)—N-(2-(10-(chloromethyl)-5-thioxo-5,8,9,10-tetrahydro-4H-pyrrolo[3',2',5,6]naphtho[1,8-de][1,3]oxazine-8-carbonyl)-1H-indol-5-yl)-1H-indole-2-carboxamide (25)

tert-butyl 10-(chloromethyl)-5-thioxo-9,10-dihydro-4H-pyrrolo[3',2',5,6]naphtho[1,8-de][1,3]oxazine-8(5H)-carboxylate (23)

$^1$H NMR (THF-d$_8$, 600 MHz) δ 11.56 (s, 1H), 7.73 (br, 1H), 7.31-7.27 (m, 3H), 6.50 (d, J=6 Hz, 1H), 4.17-4.11 (m, 2H), 3.96-3.91 (m, 2H), 3.62 (t, J=12 Hz, 1H), 1.58 (s, 9H). $^{13}$C NMR (acetone-d$_6$, 150 MHz) δ 180.9, 152.7, 151.2, 144.9, 133.9, 130.9, 130.3, 118.1, 117.0, 110.5, 104.0, 99.6, 81.9, 53.9, 47.2, 42.4 28.7. IR (film) ν$_{max}$ 2976, 2359, 1699, 1648, 1604, 1368, 1160, 1137 cm$^{-1}$. ESI-TOF HRMS m/z 399.0880 (M+H$^+$, C$_{19}$H$_{19}$ClN$_2$O$_3$S requires 391.0878).

The enantiomers were resolved on a semi-preparative Diacel chiralcel OD column (0.46 cm×25 cm) with 30% i-PrOH/hexanes elution; α=1.62.

(1S)-23: [α]$^{23}_D$−21.2 (c 1.3, THF), natural enantiomer.
(1R)-23: [α]$^{23}_D$+21.5 (c 1.2, THF), unnatural enantiomer.

$^1$H NMR (THF-d$_8$, 600 MHz) δ 11.58 (s, 1H), 11.18 (s, 1H), 11.14 (s, 1H), 9.40 (s, 1H) 8.34 (s, 1H), 8.12 (s, 1H), 7.6 (d, J=12 Hz, 1H), 7.46 (d, J=6 Hz, 1H), 7.41 (dd, J=9, 6 Hz, 1H), 7.37 (d, J=6 Hz, 1H), 7.35-7.31 (m, 2H), 7.21-7.18 (m, 2H), 7.09 (d, J=6 Hz, 1H), 7.04 (t, J=12 Hz, 1H), 6.51 (dd, J=9, 6 Hz, 1H), 4.79 (t, J=6 Hz, 1H), 4.72 (dd, J=12, 6 Hz, 1H), 4.20-4.17 (m, 1H), 3.97 (dd, J=12, 6 Hz, 1H), 3.73 (dd, J=12, 12 Hz, 1H). $^{13}$C NMR (THF-d$_8$, 150 MHz) δ 180.8, 161.3, 160.6, 150.5, 145.3, 138.1, 134.7, 133.6, 133.3, 133.1, 132.0, 130.3, 130.0, 128.9, 124.4, 122.4, 120.7, 120.2, 119.7, 117.3, 114.0, 112.9, 112.6, 111.2, 107.2, 104.5, 103.0, 101.6, 55.8, 47.0, 43.4, 30.7, 26.4. IR (film) ν$_{max}$3307, 1609, 1518, 1404, 1312, 1246, 159, 1139 cm$^{-1}$. ESI-TOF HRMS m/z 592.1211 (M+H$^+$, C$_{32}$H$_{22}$ClN$_5$O$_3$S requires 592.1205).

(1S)-25: [α]$^{23}_D$+13.0 (c 0.65, THF), natural enantiomer.
(1R)-25: [α]$^{23}_D$−13.2 (c 12.5, THF), unnatural enantiomer.

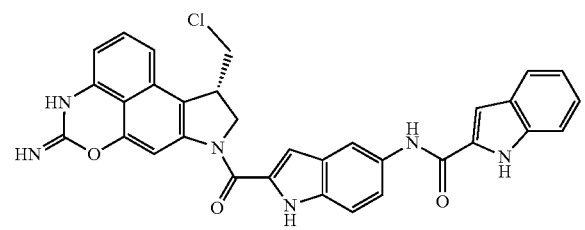 [SMILES: N=C1Nc2cccc3c4c(cc(c23)O1)N(C(=O)c1cc2cc(NC(=O)c3cc5ccccc5[nH]3)ccc2[nH]1)C[C@H]4CCl]

(S)—N-(2-(10-(chloromethyl)-5-imino-5,8,9,10-tetrahydro-4H-pyrrolo[3',2',5,6]naphtho[1,8-de][1,3]oxazine-8-carbonyl)-1H-indol-5-yl)-1H-indole-2-carboxamide (24)

$^1$H NMR (DMSO-d$_6$, 600 MHz) δ 11.82 (s, 1H), 11.74 (s, 1H), 10.19 (s, 1H), 8.25 (s, 1H), 7.72 (br), 7.68 (d, J=8.4 Hz, 1H), 7.59 (d, J=7.2 Hz, 1H), 7.49 (t, J=9 Hz, 2H), 7.43 (s, 1H), 7.34 (t, J=8.4 Hz, 1H), 7.24-7.19 (m, 5H), 7.07 (t, J=8.4 Hz, 1H), 6.55 (d, J=7.8 Hz, 1H), 4.82 (br, 1H), 4.57 (d, J=10.8 Hz, 1H), 4.16 (br, 1H), 4.03-3.94 (m, 2H). $^{13}$C NMR (DMSO-d$_6$, 150 MHz) δ 160.2, 159.5, 152.9, 149.9, 142.6, 142.2, 136.6, 133.3, 131.8, 131.7, 130.9, 130.4, 129.7, 127.04, 127.00, 123.5, 121.6, 119.8, 119.4, 117.8, 113.8, 113.1, 112.9, 112.3, 112.2, 111.1, 106.9, 105.9, 103.3, 97.3, 54.6, 47.1, 41.0. ESI-TOF HRMS m/z 575.1596 (M+H$^+$, C$_{32}$H$_{23}$ClN$_6$O$_3$ requires 575.1593).

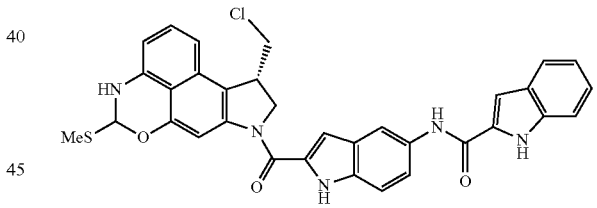

(S)—N-(2-(10-(chloromethyl)-5-(methylthio)-9,10-dihydro-8H-pyrrolo[3',2':5,6]naphtho[1,8-de][1,3]oxazine-8-carbonyl)-1H-indol-5-yl)-1H-indole-2-carboxamide (26)

$^1$H NMR (THF-d$_8$, 600 MHz) δ 11.10 (s, 1H), 11.08 (s, 1H), 9.31 (s, 1H), 8.38 (s, 1H), 7.98 (s, 1H), 7.60 (d, II=7.8 Hz, 1H), 7.50 (dd, J=7.8, 1.8 Hz, 1H), 7.45-7.24 (m, 2H), 7.40-7.37 (m, 2H), 7.20-7.15 (m, 3H), 7.03 (t, J=16.2 Hz, 1H), 6.82 (dd, J=6.6, 1.2 Hz, 1H), 4.79-4.77 (m, 2H), 4.13-4.12 (m, 1H), 3.98 (dd, J=10.8, 3 Hz, 1H), 3.71-3.69 (m, 1H), 2.54 (s, 3H). $^{13}$C NMR (THF-d$_8$, 150 MHz) δ 162.8, 161.5, 160.5, 151.3, 144.8, 139.5, 138.3, 134.8, 133.6, 132.4, 131.2, 130.9, 129.2, 124.5, 122.5, 120.8, 120.0, 119.4, 118.9, 116.2, 115.4, 113.7, 112.9, 112.7, 107.1, 102.9, 100.3, 55.9, 46.9, 43.8, 33.0, 30.8, 14.1. ESI-TOF HRMS m/z 606.1353 (M+H$^+$, C$_{33}$H$_{24}$ClN$_5$O$_3$S requires 606.1361).

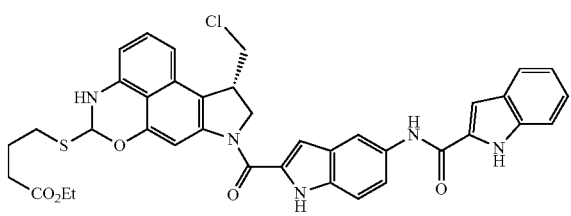 [SMILES: CCOC(=O)CCCSC1Nc2cccc3c4c(cc(c23)O1)N(C(=O)c1cc2cc(NC(=O)c3cc5ccccc5[nH]3)ccc2[nH]1)C[C@H]4CCl]

(S)-ethyl 4-((8-(5-(1H-indole-2-carboxamido)-1H-indol-2-carbonyl)-10-(chloromethyl)-9,10-dihydro-8H-pyrrolo[3',2':5,6]naphtho[1,8-de][1,3]oxazin-5-yl)thio)butanoate (27)

ESI-TOF HRMS ink 706.1876 (M+H$^+$, $C_{38}H_{32}ClN_5O_5S$ requires 706.1885).

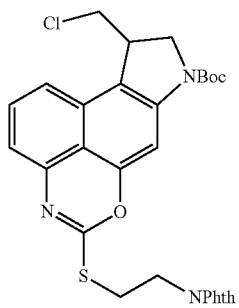

tert-butyl 10-(chloromethyl)-5-((2-(1,3-dioxoisoindolin-2-yl)ethyl)thio)-9,10-dihydro-8H-pyrrolo[3',2':5,6]naphtho[1,8-de][1,3]oxazine-8-carboxylate (28)

$^1$H NMR (THF-d$_8$, 600 MHz) δ 7.82-7.81 (m, 2H), 7.73-7.71 (m, 2H), 7.57 (br, 1H), 7.34-7.27 (m, 2H), 6.77 (d, J=7.2 Hz, 1H), 4.15-4.07 (m, 5H), 3.91-3.90 (m, 2H), 3.42 (t, J=6.6 Hz, 2H) 1.56 (s, 9H). $^{13}$C NMR (THF-d$_8$, 150 MHz) 168.5, 161.1, 152.8, 151.8, 139.3, 134.8, 133.5, 131.4, 130.8, 123.89, 123.88, 118.6, 115.4, 115.0, 98.2, 81.7, 53.7, 47.2, 37.6, 30.9, 30.8, 30.5, 28.7δ. IR (film) ν$_{max}$ 2927, 2360, 1714, 1636, 1587, 1392, 1331, 1121 cm$^{-1}$. ESI-TOF HRMS m/z 564.1354 (M+H$^+$, $C_{29}H_{26}ClN_3O_5S$ requires 564.1354).

The enantiomers were resolved on a semi-preparative Diacel chiralcel OD column (0.46 cm×25 cm) with 15% i-PrOH/hexanes elution; α=1.24.

(1S)-28: [α]$^{23}_D$ −21.2 (c 0.65, THF), natural enantiomer.
(1R)-28: [α]$^{23}_D$ +21.8 (c 0.73, THF), unnatural enantiomer.

(S)—N-(2-(10-(chloromethyl)-5-((2-(1,3-dioxoisoindolin-2-yl)ethyl)thio)-9,10-dihydro-8H-pyrrolo[3',2':5,6]naphtho[1,8-de][1,3]oxazine-8-carbonyl)-1H-indol-5-yl)-1H-indole-2-carboxamide ((+)-29)

$^1$H NMR (DMSO-d$_6$, 600 MHz) δ 11.83 (s, 1H), 11.73 (s, 1H), 10.18 (s, 1H), 8.24 (s, 1H), 7.95 (br, 1H), 7.83-7.80 (m, 3H), 7.76-7.74 (m, 2H), 7.68 (d, J=7.8 Hz, 1H), 7.59 (d, J=8.4 Hz, 1H) 7.48 (t, J=9.0 Hz, 3H), 7.43 (s, 1H), 7.40 (t, J=7.8 Hz, 2H), 7.26 (s, 1H), 7.22 (t, J=7.8, 2H), 7.07 (t, J=8.4, 2H), 6.73 (d, J=7.2 Hz, 1H). ESI-TOF HRMS m/z 765.1681 (M+H$^+$, $C_{29}H_{26}ClN_3O_5S$ requires 765.1675).

In Vivo Antitumor Activity

B6D2F1 mice were injected intraperitoneal (i.p.) with syngeneic L1210 cells (1×10$^6$) on day 0. Ten mice were randomly assigned to control vehicle or treatment groups for compounds (+)-4 and (+)-6 at doses of 60, 100, 250, and 500 μg/kg/inj for (+)-4 or 300, 1000, 3000, and 9000 μg/kg/inj for (+)-6. Compounds (+)-4 and (+)-6 were formulated in 100% DMSO, and injected i.p. on study days 1, 5, and 9. Following injection of tumor cells, animals were monitored daily and weighed two times per week. Percent survival (T/C) for treated and control groups were determined by dividing the total survival days for each treatment group by the total survival days for the control group and multiplying ×100. All animal studies were carried out in the animal facilities of The University of Kansas Medical Center with strict adherence to the guidelines of the IACUC Animal Welfare Committee of KUMC (IACUC approval #2009-1837).

DOCUMENTS CITED

1. Ichimura, M.; Ogawa, T.; Takahashi, K.; Kobayashi, E.; Kawamoto, I.; Yasuzawa, T.; Takahashi, I.; Nakano, H. Duocarmycin SA, A New Antitumor Antibiotic From *Streptomyces* sp. *J. Antibiot*. 1990, 43, 1037-1038.
2. Martin, D. G.; Biles, C.; Gerpheide, S. A.; Hanka, L. J.; Krueger, W. C.; McGovren, J. P.; Mizsak, S. A.; Neil, G. L.; Stewart, J. C.; Visser, J. CC-1065 (NSC 298223), A Potent New Antitumor Agent. Improved Production and Isolation, Characterization and Antitumor Activity. *J. Antibiot*. 1981, 34, 1119-1125.
3. Takahashi, I.; Takahashi, K.; Ichimura, M.; Morimoto, M.; Asano, K.; Kawamoto, I.; Tomita, F.; Nakano, H. Duocarmycin, A New Antitumor Antibiotic From *Streptomyces*. *J. Antibiot*. 1988, 41, 1915-1917.
4. Igarashi, Y.; Futamata, K.; Fujita, T.; Sekine, A.; Senda, H.; Naoki, H.; Furumai, T. Yatakemycin, A Novel Antifungal Antibiotic Produced by *Streptomyces* sp. TP-A0356. *J. Antibiot*. 2003, 56, 107-113.
5. For duocarmycin SA, see: (a) Boger, D. L.; Johnson, D. S.; Yun, W. (+)- and ent-(−)-Duocarmycin SA and (+)- and ent-(−)-N-BOC-DSA DNA Alkylation Properties. Alkyla-

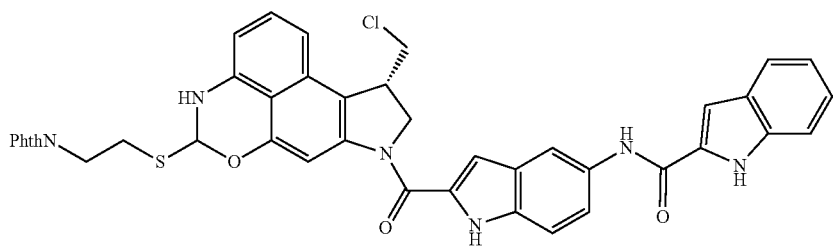

tion Site Models That Accommodate the Offset AT-Rich Adenine N3 Alkylation Selectivity of the Enantiomeric Agents. *J. Am. Chem. Soc.* 1994, 116, 1635-1656. For yatakemycin, see: (b) Parrish, J. P.; Kastrinsky, D. B.; Wolkenberg, S. E.; Igarashi, Y.; Boger, D. L. DNA Alkylation Properties of Yatakemycin. *J. Am. Chem. Soc.* 2003, 125, 10971-10976. (c) Trzupek, J. D.; Gottesfeld, J. M.; Boger, D. L. Alkylation of Duplex DNA in Nucleosome Core Particles by Duocarmycin SA and Yatakemycin. *Nat. Chem. Biol.* 2006, 2, 79-82. (d) Tichenor, M. S.; MacMillan, K. S.; Trzupek, J. D.; Rayl, T. J.; Hwang, I.; Boger, D. L. Systematic Exploration of the Structural Features of Yatakemycin Impacting DNA Alkylation and Biological Activity. *J. Am. Chem. Soc.* 2007, 129, 10858-10869. For CC-1065, see: (e) Hurley, L. H.; Lee, C.-S.; McGovren, J. P.; Warpehoski, M. A.; Mitchell, M. A.; Kelly, R. C.; Aristoff, P. A. Molecular Basis for Sequence-Specific DNA Alkylation by CC-1065. *Biochemistry* 1988, 27, 3886-3892. (f) Boger, D. L.; Johnson, D. S.; Yun, W.; Tarby, C. M. Molecular Basis for Sequence Selective DNA Alkylation by (+)- and ent-(−)-CC-1065 and Related Agents: Alkylation Site Models that Accommodate the Offset AT-Rich Adenine N3 Alkylation Selectivity. *Bioorg. Med. Chem.* 1994, 2, 115-135. (g) Boger, D. L.; Munk, S. A.; Zarrinmayeh, H. (+)-CC-1065-DNA Alkylation: Key Studies Demonstrating a Noncovalent Binding Selectivity Contribution to the Alkylation Selectivity. *J. Am. Chem. Soc.* 1991, 113, 3980-3983. (h) Boger, D. L.; Zarrinmayeh, H.; Munk, S. A.; Kitos, P. A.; Suntornwat, 0. Demonstration of a Pronounced Effect of Noncovalent Binding Selectivity on the (+)-CC-1065 DNA Alkylation and Identification of the Pharmacophore of the Alkylation Subunit. *Proc. Nat. Acad. Sci. U.S.A.* 1991, 88, 1431-1435. (i) Boger, D. L.; Coleman, R. S.; Invergo, B. J.; Sakya, S. M.; Ishizaki, T.; Munk, S. A.; Zarrinmayeh, H.; Kitos, P. A.; Thompson, S. C. Synthesis and Evaluation of Aborted and Extended CC-1065 Functional Analogs: (+)- and (−)-CPI-PDE-$I_1$, (+)- and (−)-CPI-CDPI$_1$, and (+)- and (−)-CPI-CDPI$_3$. Preparation of Key Partial Structures and Definition of an Additional Functional Role of the CC-1065 Central and Right-Hand Subunits. *J. Am. Chem. Soc.* 1990, 112, 4623-4632. For duocarmycin A, see: (j) Boger, D. L.; Ishizaki, T.; Zarrinmayeh, H.; Munk, S. A.; Kitos, P. A.; Suntornwat, O. Duocarmycin-Pyrindamycin DNA Alkylation Properties and Identification, Synthesis, and Evaluation of Agents Incorporating the Pharmacophore of the Duocarmycin-Pyrindamycin Alkylation Subunit. Identification of the CC-1065 Duocarmycin Common Pharmacophore. *J. Am. Chem. Soc.* 1990, 112, 8961-8971. (k) Boger, D. L.; Ishizaki, T.; Zarrinmayeh, H. Isolation and Characterization of the Duocarmycin-Adenine DNA Adduct. *J. Am. Chem. Soc.* 1991, 113, 6645-6649. (l) Boger, D. L.; Yun, W.; Terashima, S.; Fukuda, Y.; Nakatani, K.; Kitos, P. A.; Jin, Q. DNA Alkylation Properties of the Duocarmycins: (+)-Duocarmycin A, epi-(+)-Duocarmycin A, ent-(−)-Duocarmycin A and epi,ent-(−)-Duocarmycin A. *Bioorg. Med. Chem. Lett.* 1992, 2, 759-765. (k) Boger, D. L.; Yun, W. Reversibility of the Duocarmycin A and SA DNA Alkylation Reaction. *J. Am. Chem. Soc.* 1993, 115, 9872-9873.

6. Reviews: (a) Boger, D. L.; Johnson, D. S. CC-1065 and the Duocarmycins: Understanding Their Biological Function Through Mechanistic Studies. *Angew. Chem., Int. Ed. Engl.* 1996, 35, 1438-1474. (b) Boger, D. L. The Duocarmycins: Synthetic and Mechanistic Studies. *Acc. Chem. Res.* 1995, 28, 20-29. (c) Boger, D. L.; Johnson, D. S. CC-1065 and the Duocarmycins: Unraveling the Keys to a New Class of Naturally Derived DNA Alkylating Agents. *Proc. Natl. Acad. Sci. U.S.A.* 1995, 92, 3642-3649. (d) Boger, D. L.; Garbaccio, R. M. Shape-Dependent Catalysis: Insights into the Source of Catalysis for the CC-1065 and Duocarmycin DNA Alkylation Reaction. *Acc. Chem. Res.* 1999, 32, 1043-1052. (e) Tichenor, M. S.; Boger, D. L. Yatakemycin: Total Synthesis, DNA Alkylation, and Biological Properties. *Natural Prod. Rep.* 2008, 25, 220-226. (f) MacMillan, K. S.; Boger, D. L. Fundamental Relationships Between Structure, Reactivity, and Biological Activity for the Duocarmycins and CC-1065. *J. Med. Chem.* 2009, 52, 5771-5780. (g) Searcey, M. Duocarmycins: Nature's Prodrugs? *Curr. Pharm. Des.* 2002, 8, 1375-1389. (h) Tse, W. C.; Boger, D. L. Sequence-Selective DNA Recognition: Natural Products and Nature's Lessons. *Chem. Biol.* 2004, 11, 1607-1617.

7. (a) Boger, D. L.; Coleman, R. S. Total Synthesis of (+)-CC-1065 and ent-(−)-CC-1065. *J. Am. Chem. Soc.* 1988, 110, 1321-1323. (b) Boger, D. L.; Coleman, R. S. Total Synthesis of CC-1065, and the Precise, Functional Agent CPI-CDPI$_2$. *J. Am. Chem. Soc.* 1988, 110, 4796-4807. (c) Boger, D. L.; Machiya, K. Total Synthesis of (+)-Duocarmycin SA. *J. Am. Chem. Soc.* 1992, 114, 10056-10058. (d) Boger, D. L.; Machiya, K.; Hertzog, D. L.; Kitos, P. A.; Holmes, D. Total Synthesis and Preliminary Evaluation of (+)- and ent-(−)-Duocarmycin SA. *J. Am. Chem. Soc.* 1993, 115, 9025-9036. (e) Boger, D. L.; McKie, J. A.; Nishi, T.; Ogiku, T. Enantioselective Total Synthesis of (+)-Duocarmycin A, epi-(+)-Duocarmycin A, and Their Unnatural Enantiomers. *J. Am. Chem. Soc.* 1996, 118, 2301-2302. (f) Boger, D. L.; McKie, J. A.; Nishi, T.; Ogiku, T. Total Synthesis of (+)-Duocarmycin A and epi-(+)-Duocarmycin A and Their Unnatural Enantiomers: Assessment of Chemical and Biological Properties. *J. Am. Chem. Soc.* 1997, 119, 311-325. (g) Tichenor, M. S.; Kastrinsky, D. B.; Boger, D. L. Total Synthesis, Structure Revision, and Absolute Configuration of (+)-Yatakemycin. *J. Am. Chem. Soc.* 2004, 126, 8396-8398. (h) Tichenor, M. S.; Trzupek, J. D.; Kastrinsky, D. B.; Shiga, F.; Hwang, I.; Boger, D. L. Asymmetric Total Synthesis of (+)- and ent-(−)-Yatakemycin and Duocarmycin SA. Evaluation of Yatakemycin Key Partial Structures and Its Unnatural Enantiomer. *J. Am. Chem. Soc.* 2006, 128, 15683-15696. (i) MacMillan, K. S.; Nguyen, T.; Hwang, I.; Boger, D. L. Total Synthesis and Evaluation of iso-Duocarmycin SA and iso-Yatakemycin. *J. Am. Chem. Soc.* 2009, 131, 1187-1194.

8. (a) Boger, D. L.; Hertzog, D. L.; Bollinger, B.; Johnson, D. S.; Cai, H.; Goldberg, J.; Turnbull, P. Duocarmycin SA Shortened, Simplified, and Extended Agents: A Systematic Examination of the Role of the DNA Binding Subunit. *J. Am. Chem. Soc.* 1997, 119, 4977-4986. (b) Boger, D. L.; Bollinger, B.; Hertzog, D. L.; Johnson, D. S.; Cai, H.; Mesini, P.; Garbaccio, R. M.; Jin, Q.; Kitos, P. A. Reversed and Sandwiched Analogs of Duocarmycin SA: Establishment of the Origin of the Sequence-Selective Alkylation of DNA and New Insights into the Source of Catalysis. *J. Am. Chem. Soc.* 1997, 119, 4987-4998. (c) Boger, D. L.; Garbaccio, R. M. Catalysis of the CC-1065 and Duocarmycin DNA Alkylation Reaction: DNA Binding Induced Conformational Change in the Agent Results in Activation. *Bioorg. Med. Chem.* 1997, 5, 263-276.

9. (a) Boger, D. L.; Ishizaki, T.; Kitos, P. A.; Suntornwat, 0. Synthesis of N-(tert-Butyloxycarbonyl)-CBI, CBI, CBI-CDPI$_1$, and CBI-CDPI$_2$: Enhanced Functional Analogs of CC-1065 Incorporating the 1,2,9,9a-Tetrahydrocyclopropa[c]benz[e]indol-4-one (CBI) Left-Hand Subunit. *J. Org. Chem.* 1990, 55, 5823-5832. (b) Boger, D. L.; Ishizaki, T.; Wysocki, R. J., Jr.; Munk, S. A.; Kitos, P. A.;

Suntornwat, O. Total Synthesis and Evaluation of (±)-N-(tert-Butoxycarbonyl)-CBI, (±)-CBI-CDPI$_1$, and (±)-CBI-CDPI$_2$: CC-1065 Functional Agents Incorporating the Equivalent 1,2,9,9a-Tetrahydrocyclopropa[1,2-c]benz[1,2-e]indol-4-one (CBI) Left-Hand Subunit. *J. Am. Chem. Soc.* 1989, 111, 6461-6463. (c) Boger, D. L.; Ishizaki, T. Resolution of a CBI Precursor and Incorporation into the Synthesis of (+)-CBI, (+)-CBI-CDPI$_1$, (+)-CBI-CDPI$_2$: Enhanced Functional Analogs of (+)-CC-1065. A Critical Appraisal of a Proposed Relationship Between Electrophile Reactivity, DNA Binding Properties, and Cytotoxic Potency. *Tetrahedron Lett.* 1990, 31, 793-796. (d) Boger, D. L.; Ishizaki, T.; Zarrinmayeh, H.; Kitos, P. A.; Suntornwat, O. A Potent, Simple Derivative of an Analog of the CC-1065 Alkylation Subunit. *Bioorg. Med. Chem. Lett.* 1991, 1, 55-58. (e) Boger, D. L.; Munk, S. A. DNA Alkylation Properties of Enhanced Functional Analogs of CC-1065 Incorporating the 1,2,9,9a-Tetrahydro-cyclopropa[1,2-c]benz[1,2-e]indol-4-one (CBI) Alkylation Subunit. *J. Am. Chem. Soc.* 1992, 114, 5487-5496. (f) Boger, D. L.; Yun, W. Role of the CC-1065 and Duocarmycin N$^2$ Substituent: Validation of a Direct Relationship Between Solvolysis Chemical Stability and in vitro Biological Potency. *J. Am. Chem. Soc.* 1994, 116, 5523-5524. (g) Boger, D. L.; Yun, W.; Cai, H.; Han, N. CBI-CDPBO$_1$ and CBI-CDPBI$_1$: CC-1065 Analogs Containing Deep-Seated Modifications in the DNA Binding Subunit. *Bioorg. Med. Chem.* 1995, 3, 761-775. (h) Boger, D. L.; Yun, W. CBI-TMI: Synthesis and Evaluation of a Key Analog of the Duocarmycins. Validation of a Direct Relationship between Chemical Solvolytic Stability and Cytotoxic Potency and Confirmation of the Structural Features Responsible for the Distinguishing Behavior of Enantiomeric Pairs of Agents. *J. Am. Chem. Soc.* 1994, 116, 7996-8006. (i) Parrish, J. P.; Katrinsky, D. B.; Stauffer, F.; Hedrick, M. P.; Hwang, I.; Boger, D. L. Establishment of Substitution Effects in the DNA Binding Subunit of CBI Analogues of the Duocarmycins and CC-1065. *Bioorg. Med. Chem.* 2003, 11, 3815-3838.

10. (a) Boger, D. L.; Yun, W.; Teegarden, B. R. An Improved Synthesis of 1,2,9,9a-Tetrahydrocyclopropa[c]benz[e]indol-4-one (CBI): A Simplified Analog of the CC-1065 Alkylation Subunit. *J. Org. Chem.* 1992, 57, 2873-2876. (b) Boger, D. L.; McKie, J. A. An Efficient Synthesis of 1,2,9,9a-Tetrahydrocyclopropa[c]benz[e]indol-4-one (CBI): An Enhanced and Simplified Analog of the CC-1065 and Duocarmycin Alkylation Subunits. *J. Org. Chem.* 1995, 60, 1271-1275. (c) Boger, D. L.; McKie, J. A.; Boyce, C. W. Asymmetric Synthesis of the 1,2,9,9a-Tetrahydrocyclopropa[c]benz[e]indol-4-one (CBI) Alkylation Subunit of CC-1065 and Duocarmycin Analogues. *Synlett* 1997, 515-517. (d) Kastrinsky, D. B.; Boger, D. L. Effective Asymmetric Synthesis of 1,2,9,9a-Tetrahydrocyclopropa[e]benz[e]indol-4-one (CBI). *J. Org. Chem.* 2004, 69, 2284-2289. (e) Lajiness, J. P.; Boger, D. L. Asymmetric Synthesis of 1,2,9,9a-Tetrahydrocyclopropa[c]benz[e]indol-4-one (CBI). *J. Org. Chem.* 2010, 76, 583-587.

11. (a) Boger, D. L.; Yun, W.; Han, N. 1,2,9,9a-Tetrahydrocyclopropa[c]benz[e]indol-4-one (CBI) Analogs of CC-1065 and the Duocarmycins: Synthesis and Evaluation. *Bioorg. Med. Chem.* 1995, 3, 1429-1453. (b) Boger, D. L.; Ishizaki, T.; Sakya, S.; Munk, S. A.; Kitos, P. A.; Jin, Q.; Besterman, J. M. Synthesis and Preliminary Evaluation of (+)-CBI-indole$_2$: An Enhanced Functional Analog of CC-1053. *Bioorg. Med. Chem. Lett.*, 1991, 1, 115-120.

12. For Carzelesin, see: (a) Li, L.; DeKoning, T. F.; Kelly, R. C.; Krueger, W. C.; McGovren, J. P.; Padbury, G. E.; Petzold, G. L.; Wallace, T. L.; Ouding, R. J.; Prairie, M. D.; Gebhard, I. Cytotoxicity and Antitumor Activity of Carzelesin, a Prodrug Cyclopropylpyrroloindole Analogue. *Cancer Res.* 1992, 52, 4904-4913. (b) van Tellingen, O; Nooijen, W. J.; Schaaf, L. J.; van der Valk, M.; van Asperen, J.; Henrar, R. E. C.; Beijnen, J H. Comparative Pharmacology of the Novel Cyclopropylpyrroloindole-Prodrug Carzelesin in Mice, Rats, and Humans. *Cancer Res.* 1998, 58, 2410-2416. For KW-2189, see: (c) Kobayashi, E.; Okamoto, A.; Asada, M.; Okabe, M.; Nagamura, S.; Asai, A.; Saito, H.; Gomi, K.; Hirata, T. Characteristics of Antitumor Activity of KW-2189, A Novel Water-Soluble Derivative of Duocarmycin, Against Murine and Human Tumors. *Cancer Res.* 1994, 54, 2404-2410. (d) Nagamura, S.; Kanda, Y.; Kobayashi, E.; Gomi, K.; Saito, H. Synthesis and Antitumor Activity of Duocarmycin Derivatives. *Chem. Pharm. Bull.* 1995, 43, 1530-1535. For other CBI carbamate prodrugs: (e) Boger, D. L.; Boyce, C. W.; Garbaccio, R. M.; Searcey, M.; Jin, Q. CBI Prodrug Analogs of CC-1065 and the Duocarmycins. *Synthesis* 1999, 1505-1509. (f) Li, L. S.; Sinha, S. C. Studies Toward the Duocarmycin Prodrugs for the Antibody Prodrug Therapy Approach. *Tetrahedron Lett.* 2009, 50, 2932-2935.

13. For glycosidic prodrugs: (a) Tietze, L. F.; Lieb, M.; Herzig, T.; Haunert, F.; Schuberth, I. A Strategy for Tumor-Selective Chemotherapy by Enzymatic Liberation of seco-duocarmycin SA-derivatives from Nontoxic Prodrugs. *Bioorg. Med. Chem.* 2001, 9, 1929-1939. (b) Tietze, L. F.; Major, F.; Schuberth, I. Antitumor Agents: Development of Highly Potent Glycosidic Duocarmycin Analogues for Selective Cancer Therapy. *Angew. Chem. Int. Ed.* 2006, 45, 6574-6577. (c) Tietze, L. F.; Schuster, H. J.; Schmuck, K.; Schuberth, I.; Alves, F. Duocarmycin-based Prodrugs for Cancer Prodrug Monotherapy. *Bioorg. Med. Chem.* 2008, 16, 6312-6318. For reductively activated prodrugs: (d) Hay, M. P.; Anderson, R. F.; Ferry, D. M.; Wilson, W. R.; Denny, W. A. Synthesis and Evaluation of Nitroheterocyclic Carbamate Prodrugs for Use with Nitroreductase-Mediated Gene-Directed Enzyme Prodrug Therapy. *J. Med. Chem.* 2003, 46, 5533-5545. (e) Hay, M. P.; Sykes, B. M.; Denny, W. A.; Wilson, W. R. A 2-Nitroimidazole Carbamate Prodrug of 5-Amino-1-(chloromethyl)-3-[(5,6,7-trimethoxyindol-2-yl)carbonyl]-1,2-dihydro-3H-benz[e]indole (Amino-seco-CBI-TMI) for Use With ADEPT and GDEPT. *Bioorg. Med. Chem. Lett.* 1999, 9, 2237-2242. (f) Tercel, M.; Atwell, G. J.; Yang, S.; Ashoorzadeh, A.; Stevenson, R. J.; Botting, K. J.; Gu, Y.; Mehta, S. Y.; Denny, W. A.; Wilson, W. R.; Pruijn, F. B. Selective Treatment of Hypoxic Tumor Cells In Vivo: Phosphate Pre-Prodrugs of Nitro Analogues of the Duocarmycins. *Angew. Chem. Int. Ed.* 2011, 50, 2606-2609. (g) Townes, H.; Summerville, K.; Purnell, B.; Hooker, M.; Madsen, E.; Hudson, S.; Lee, M. Investigation of a Novel Reductively-Activatable Anticancer Prodrug of seco-CBI-TMI, an Analog of Duocarmycin SA. *Med. Chem. Res.* 2002, 11, 248-253. (h) Boger, D. L.; Garbaccio, R. M. A Novel Class of CC-1065 and Duocarmycin Analogues Subject to Mitomycin-Related Reductive Activation. *J. Org. Chem.* 1999, 64, 8350-8362. For other prodrugs: (1) Wang, Y.; Li, L.; Tian, Z.; Jiang, W.; Larrick, J. Synthesis and Antitumor Activity of CBI-Bearing Ester and Carbamate Prodrugs of CC-1065. *Bioorg. Med. Chem.* 2006, 14, 7854-7861. (j) Zhao, R. H; Erickson, H. K.; Leece, B. A.; Reid, E. E.; Goldmacher, V. S.; Lambert, J. M.; Chari, R. V. J. Synthesis and Biological Evaluation of Antibody Conjugates of Phosphate Prodrugs of Cytotoxic DNA Alkylators for the Targeted Treatment of Cancer. *J. Med. Chem.* 2012, 55, 766-782.

14. (a) Jin, W.; Trzupek, J. D.; Rayl, T. J.; Broward, M. A.; Vielhauer, G. A.; Weir, S. J.; Hwang, I.; Boger, D. L. A Unique Class of Duocarmycin and CC-1065 Analogues Subject to Reductive Activation. *J. Am. Chem. Soc.* 2007, 129, 15391-15397. (b) Lajiness, J. P.; Robertson, W. M.; Dunwiddie, I.; Broward, M. A.; Vielhauer, G. A.; Weir, S. J.; Boger, D. L. Design, Synthesis, and Evaluation of Duocarmycin O-Amino Phenol Prodrugs Subject to Tunable Reductive Activation. *J. Med. Chem.* 2010, 53, 7731-7738.
15. Wolkenberg, S. E.; Boger, D. L. Mechanisms of in situ Activation for DNA Targeting Antitumor Agents. *Chem. Rev.* 2002, 102, 2477-2495.
16. Boger, D. L.; Boyce, C. W.; Garbaccio, R. M.; Goldberg, J. A. CC-1065 and the Duocarmycins: Synthetic Studies. *Chem. Rev.* 1997, 97, 787-828.
17. Boger, D. L.; Han, N.; Tarby, C. M.; Boyce, C. W.; Cai, H.; Jin, Q.; Kitos, P. A. Synthesis, Chemical Properties, and Preliminary Evaluation of Substituted CBI Analogs of CC-1065 and the Duocarmycins Incorporating the 7-Cyano-1,2,9,9a-tetrahydrocyclopropa[c]benz[e]indol-4-one Alkylation Subunit: Hammett Quantitation of the Magnitude of Electronic Effects on Functional Reactivity. *J. Org. Chem.* 1996, 61, 4894-4912.
18. Boger, D. L.; Boyce, C. W.; Garbaccio, R. M.; Searcey, M. Synthesis of CC-1065 and Duocarmycin Analogs via Intramolecular Aryl Radical Cyclization of a Tethered Vinyl Chloride. *Tetrahedron Lett.* 1998, 39, 2227-2230.
19. Boger, D. L.; Brotherton, C. E. Total Synthesis of Azafluoranthene Alkaloids: Refescine and Imelutine. *J. Org. Chem.* 1984, 49, 4050-4055.
20. Wolfe, A. L. unpublished studies.
21. Huang, X.; Buchwald, S. L. New Ammonia Equivalents for the Pd-Catalyzed Amination of Aryl Halides. *Org. Lett.* 2001, 3, 3417-3419.
22. (a) Boger, D. L.; Panek, J. S. Palladium(0)-Mediated 13-Carboline Synthesis: Preparation of the CDE Ring System of Lavendamycin. *Tetrahedron Lett.* 1984, 25, 3175-3178. (b) Boger, D. L.; Duff, S. R.; Panek, J. S.; Yasuda, M. Inverse Electron Demand Diels-Alder Reactions of Heterocyclic Azadienes. Studies on the Total Synthesis of Lavendamycin: Investigative Studies on the Preparation of the CDE 13-Carboline Ring System and AB Quinoline-5, 8-quinone Ring System. *J. Org. Chem.* 1985, 50, 5782-5789. (c) Boger, D. L.; Panek, J. S.; Duff, S. R.; Yasuda, M. Total Synthesis of Lavendamycin Methyl Ester. *J. Org. Chem.* 1985, 50, 5790-5795.
23. Boger, D. L.; Munk, S. A.; Zarrimayeh, H.; Ishizaki, T.; Haught, J.; Bina, M. An Alternative and Convenient Strategy for Generation of Substantial Quantities of Singly 5'-P$^{32}$-End-Labeled Double-Stranded DNA for Binding Studies. Development of a Protocol for Examination of Functional Features of (+)-CC-1065 and the Duocarmycins That Contribute to Their Sequence-Selective DNA Alkylation Properties. *Tetrahedron* 1991, 47, 2661-2682.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:
1. A compound of formula (I)

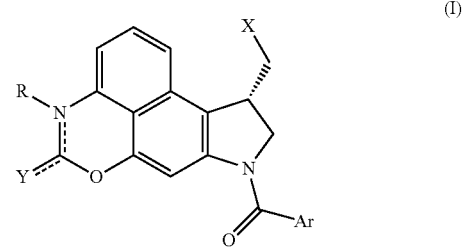

wherein a dotted line indicates a double bond or a single bond, provided that when the N has a double bond thereto, R is absent;

X is a leaving group,

Y is O, S, SR, or NR, each R is independently H, $(C_1-C_6)$alkyl, or substituted $(C_1-C_6)$alkyl, and Ar is heteroaryl optionally substituted by one or more substituents J;

J is selected from the group consisting of F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_1$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R'), N(R')C(S)N(R')$_2$, N(COR')COR', N(OR')R', C(=NH)N(R')$_2$, C(O)N(OR')R' and C(=NOR')R'; wherein R' is selected from the group consisting of hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, and heteroarylalkyl;

or any salt thereof, or a hydrate thereof.

2. The compound of claim 1 wherein Y is O.
3. The compound of claim 1 wherein Y is NH.
4. The compound of claim 1 wherein Y is S.
5. The compound of claim 1 wherein Y is SR, wherein R is $(C_1-C_6)$alkyl, or substituted $(C_1-C_6)$alkyl.
6. The compound of claim 1 wherein X is a halo or a sulfonic ester.
7. The compound of claim 1 wherein X is a chloro or a mesylate.
8. The compound of claim 1 wherein R is H.
9. The compound of claim 1 wherein Ar comprises an indole bonded at an indole 2-position.
10. The compound of claim 9 wherein the indole is further substituted with a heteroarylamino group.
11. The compound of claim 10 wherein the heteroaroylamino group is an unsubstituted or a substituted 2-indoloylamino group.

12. The compound of claim 1 of formula
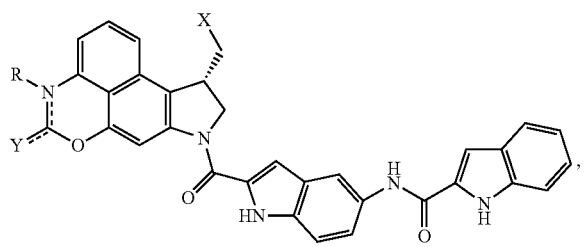
wherein R, X, and Y are as defined in claim 1; or any salt thereof, or a hydrate thereof.
13. The compound of claim 1 of formula
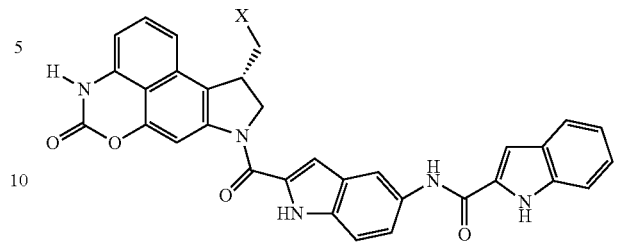
wherein X is as defined in claim 1.
14. The compound of claim 1 of any one of the following formulae
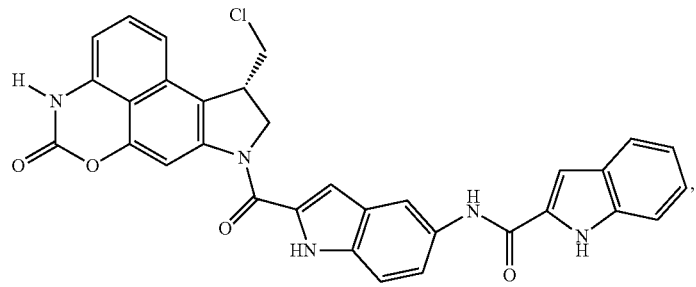
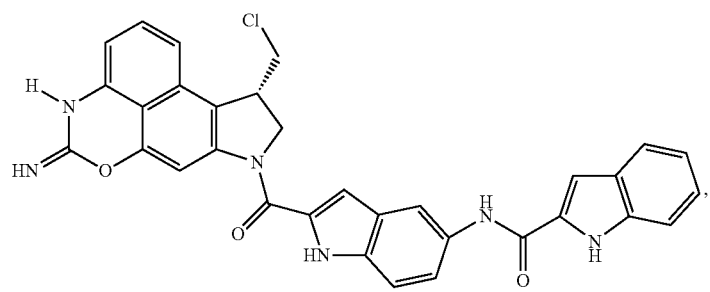
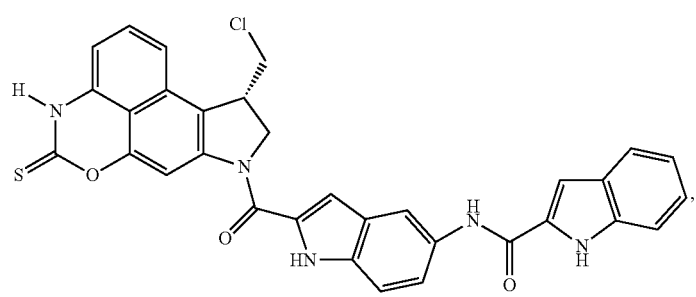
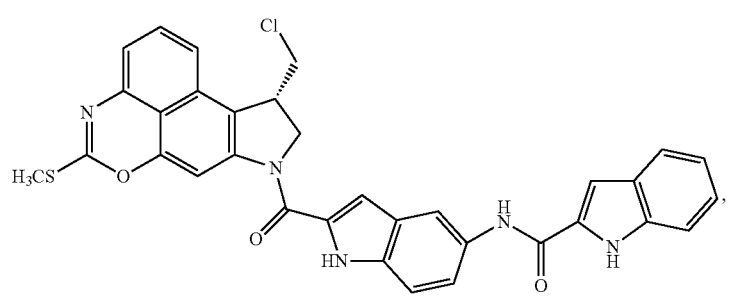

-continued
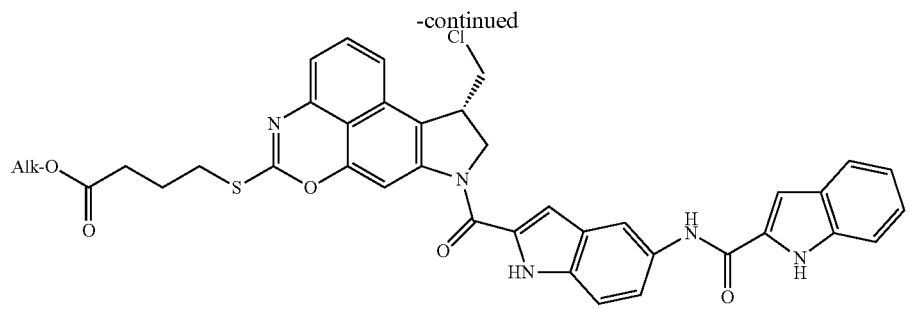
wherein Alk is (C₁-C₆)alkyl, or,
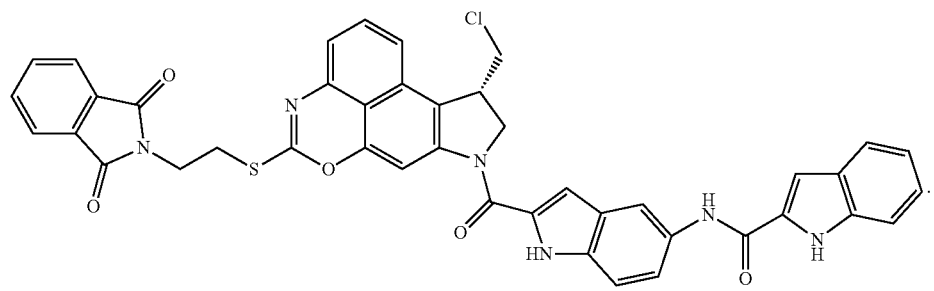 [SMILES: O=C(Nc1ccc2[nH]c(C(=O)N3C[C@@H](CCl)c4c3cc3c5c(cccc45)N=C(SCCN4C(=O)c5ccccc5C4=O)O3)cc2c1)c1cc2ccccc2[nH]1]
15. A pharmaceutical composition comprising a compound of claim 1 and a pharmaceutically acceptable excipient.
16. A synthetic intermediate for preparation of a compound of formula (I) of claim 1, of formula (III)
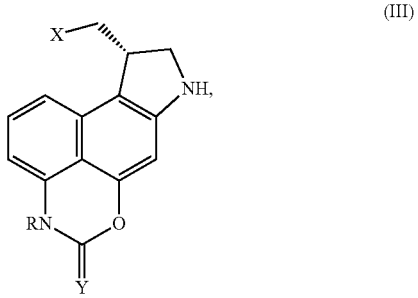
wherein R, X, and Y, are as defined in claim 1, or an enantiomer thereof.
17. A compound of formula
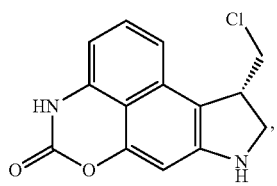 [SMILES: O=C1Nc2cccc3c4c(cc(c23)O1)NC[C@H]4CCl]
or an enantiomer thereof.
* * * * *